(12) United States Patent
Knoepfle et al.

(10) Patent No.: US 9,801,671 B2
(45) Date of Patent: Oct. 31, 2017

(54) FIXATION ASSEMBLY WITH MULTIPLE SECTIONS FOR SECURING PARTS OF A STERNUM

(71) Applicant: Stryker European Holdings I, LLC, Kalamazoo, MI (US)

(72) Inventors: Christian Knoepfle, Donaueschingen (DE); Karl Greiner, Muehlheim (DE); Manfred Schmuck, Muehlheim (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 590 days.

(21) Appl. No.: 14/327,909

(22) Filed: Jul. 10, 2014

(65) Prior Publication Data

US 2015/0018830 A1    Jan. 15, 2015

Related U.S. Application Data

(60) Provisional application No. 61/845,024, filed on Jul. 11, 2013.

(30) Foreign Application Priority Data

Aug. 5, 2013   (EP) .................................... 13003896

(51) Int. Cl.
*A61B 17/56* (2006.01)
*A61B 17/58* (2006.01)
(Continued)

(52) U.S. Cl.
CPC ........ *A61B 17/823* (2013.01); *A61B 17/8057* (2013.01); *A61B 17/8076* (2013.01);
(Continued)

(58) Field of Classification Search
None
See application file for complete search history.

(56) References Cited

U.S. PATENT DOCUMENTS

| 1,616,232 A | 2/1927 | Roberts et al. |
| 3,926,193 A | 12/1975 | Hasson |

(Continued)

FOREIGN PATENT DOCUMENTS

| CA | 2286111 A1 | 10/1998 |
| CA | 2439094 A1 | 9/2002 |

(Continued)

OTHER PUBLICATIONS

International Search Report and Written Opinion for Application No. PCT/EP2013/066408 dated Oct. 22, 2013.

(Continued)

*Primary Examiner* — Sameh Boles
(74) *Attorney, Agent, or Firm* — Lerner, David, Littenberg, Krumholz & Mentlik, LLP

(57) ABSTRACT

A fixation assembly for securing parts of a sternum has a first section having a first attachment structure for securing the first section to a first sternum part. The fixation assembly includes a second section having a second attachment structure for securing the second section to a second sternum part. A mating arrangement is provided defining a mating direction and a predetermined relative position between the first and second sections in a plane perpendicular to the mating direction. At least one holding member is provided for detachably holding the first and second sections in an abutting relationship in the predetermined relative position. This may be achieved in one variant by simultaneous engagement of the first and second sections substantially along the mating direction.

14 Claims, 13 Drawing Sheets

(51) Int. Cl.
    *A61B 17/80*     (2006.01)
    *A61F 2/30*     (2006.01)
    *A61B 17/82*     (2006.01)
    *A61B 17/00*     (2006.01)
    *A61B 17/06*     (2006.01)

(52) U.S. Cl.
    CPC ............... *A61B 2017/00004* (2013.01); *A61B 2017/06176* (2013.01)

(56) References Cited

U.S. PATENT DOCUMENTS

| | | |
|---|---|---|
| 4,201,215 A | 5/1980 | Crossett et al. |
| 4,279,248 A | 7/1981 | Gabbay |
| 4,512,346 A | 4/1985 | Lemole |
| 4,583,541 A | 4/1986 | Barry |
| 4,802,477 A | 2/1989 | Gabbay |
| 4,944,753 A | 7/1990 | Burgess et al. |
| 5,047,034 A | 9/1991 | Sohngen |
| 5,053,212 A | 10/1991 | Constantz et al. |
| 5,139,498 A | 8/1992 | Astudillo Ley |
| 5,164,187 A | 11/1992 | Constantz et al. |
| 5,188,670 A | 2/1993 | Constantz |
| 5,279,831 A | 1/1994 | Constantz et al. |
| 5,417,698 A | 5/1995 | Green et al. |
| 5,827,286 A | 10/1998 | Incavo et al. |
| 5,941,881 A | 8/1999 | Barnes |
| 5,964,763 A | 10/1999 | Incavo et al. |
| 5,964,932 A | 10/1999 | Ison et al. |
| 5,968,253 A | 10/1999 | Poser et al. |
| 6,007,538 A | 12/1999 | Levin |
| 6,051,007 A | 4/2000 | Hogendijk et al. |
| 6,053,970 A | 4/2000 | Ison et al. |
| 6,200,318 B1 | 3/2001 | Har-Shai et al. |
| 6,217,580 B1 | 4/2001 | Levin |
| 6,302,899 B1 | 10/2001 | Johnson et al. |
| 6,540,769 B1 | 4/2003 | Miller, III |
| 6,558,709 B2 | 5/2003 | Higham |
| 6,596,338 B2 | 7/2003 | Scott et al. |
| 6,821,528 B2 | 11/2004 | Scott et al. |
| 6,872,210 B2 | 3/2005 | Hearn |
| 6,969,398 B2 | 11/2005 | Stevens et al. |
| 7,033,377 B2 | 4/2006 | Miller, III |
| 7,635,364 B2 | 12/2009 | Barrall et al. |
| 7,695,473 B2 | 4/2010 | Ralph et al. |
| 7,740,649 B2 | 6/2010 | Mosca et al. |
| 7,871,411 B2 | 1/2011 | Grevious |
| 8,221,421 B2 | 7/2012 | Hearn |
| 8,460,295 B2 | 6/2013 | McClellan et al. |
| 8,486,114 B2 | 7/2013 | Gillard et al. |
| 2002/0077659 A1 | 6/2002 | Johnson et al. |
| 2002/0128654 A1 | 9/2002 | Steger et al. |
| 2002/0143336 A1* | 10/2002 | Hearn ................ A61B 17/8009 606/246 |
| 2003/0049324 A1 | 3/2003 | Vogt et al. |
| 2003/0077381 A1 | 4/2003 | Scott et al. |
| 2003/0083694 A1 | 5/2003 | Miller |
| 2003/0212399 A1 | 11/2003 | Dinh et al. |
| 2004/0010256 A1 | 1/2004 | Gabbay |
| 2004/0133206 A1 | 7/2004 | Stevens et al. |
| 2005/0070928 A1 | 3/2005 | Heino et al. |
| 2005/0124996 A1 | 6/2005 | Hearn |
| 2005/0267475 A1 | 12/2005 | Miller |
| 2006/0116683 A1 | 6/2006 | Barrall et al. |
| 2006/0122611 A1 | 6/2006 | Morales et al. |
| 2006/0134160 A1 | 6/2006 | Troczynski et al. |
| 2006/0161161 A1 | 7/2006 | Shifrin et al. |
| 2006/0195101 A1 | 8/2006 | Stevens |
| 2006/0259141 A1 | 11/2006 | Roman et al. |
| 2006/0276794 A1 | 12/2006 | Stern |
| 2007/0038218 A1 | 2/2007 | Grevious |
| 2007/0043371 A1 | 2/2007 | Teague et al. |
| 2007/0213832 A1 | 9/2007 | Wen |
| 2007/0259101 A1 | 11/2007 | Kleiner et al. |
| 2008/0154312 A1 | 6/2008 | Colleran et al. |
| 2008/0221578 A1 | 9/2008 | Zeitani |
| 2008/0306579 A1 | 12/2008 | Dolan et al. |
| 2009/0118774 A1 | 5/2009 | Miller, III |
| 2009/0118775 A1 | 5/2009 | Burke |
| 2009/0138054 A1 | 5/2009 | Teague et al. |
| 2009/0234357 A1 | 9/2009 | Morales et al. |
| 2009/0234358 A1 | 9/2009 | Morales et al. |
| 2009/0248091 A1 | 10/2009 | Teague et al. |
| 2009/0269480 A1 | 10/2009 | Berglund |
| 2010/0094294 A1 | 4/2010 | Gillard et al. |
| 2010/0179600 A1 | 7/2010 | Steger et al. |
| 2010/0305569 A1 | 12/2010 | Leuenberger et al. |
| 2011/0125193 A1 | 5/2011 | Grevious |
| 2011/0166612 A1 | 7/2011 | Bardaji Pascual et al. |
| 2011/0295257 A1 | 12/2011 | McClellan et al. |
| 2011/0313474 A1 | 12/2011 | Gabele |
| 2013/0338719 A1 | 12/2013 | Madjarov |
| 2014/0100573 A1 | 4/2014 | Llas Vargas et al. |
| 2014/0142638 A1 | 5/2014 | Goodwin et al. |

FOREIGN PATENT DOCUMENTS

| | | |
|---|---|---|
| CN | 101537208 A | 9/2009 |
| CN | 202235628 U | 5/2012 |
| DE | 202004021763 U1 | 9/2010 |
| DE | 102010021737 A1 | 11/2011 |
| DE | 102011109677 A1 | 2/2013 |
| EP | 0238219 A1 | 9/1987 |
| EP | 0597259 A2 | 5/1994 |
| EP | 0608592 A1 | 8/1994 |
| EP | 0806212 A1 | 11/1997 |
| EP | 1099416 A2 | 5/2001 |
| EP | 1121058 A1 | 8/2001 |
| EP | 1521552 A1 | 4/2005 |
| EP | 1365693 B1 | 1/2006 |
| EP | 1429674 B1 | 3/2006 |
| EP | 1654994 A1 | 5/2006 |
| EP | 1691702 A1 | 8/2006 |
| EP | 1732460 B1 | 5/2010 |
| EP | 1885268 B1 | 7/2010 |
| EP | 2063799 B1 | 9/2010 |
| EP | 2367489 A1 | 9/2011 |
| EP | 1748738 B1 | 10/2011 |
| WO | 9004366 A1 | 5/1990 |
| WO | 9505782 A1 | 3/1995 |
| WO | 9844850 A1 | 10/1998 |
| WO | 0022992 A1 | 4/2000 |
| WO | 02/067795 A1 | 9/2002 |
| WO | 03037201 A1 | 5/2003 |
| WO | 2004006784 A1 | 1/2004 |
| WO | 2004078218 A2 | 9/2004 |
| WO | 2005055844 A1 | 6/2005 |
| WO | 2005117726 A2 | 12/2005 |
| WO | 2006135935 A1 | 12/2006 |
| WO | 2007084238 A2 | 7/2007 |
| WO | 2008034537 A1 | 3/2008 |
| WO | 2009100792 A2 | 8/2009 |
| WO | 2010024946 A1 | 3/2010 |
| WO | 2010042946 A1 | 4/2010 |
| WO | 2010126436 A1 | 11/2010 |
| WO | 2011153676 A1 | 12/2011 |
| WO | 2013013218 A2 | 1/2013 |
| WO | 2013067049 A1 | 5/2013 |
| WO | 2013072576 A1 | 5/2013 |
| WO | 2014081574 A1 | 5/2014 |
| WO | 2014144479 A1 | 9/2014 |

OTHER PUBLICATIONS

International Preliminary Report on Patentability Chapter II, for Application No. PCT/EP2013/066408 dated Sep. 25, 2015.
European Search Report for EP 13003896.1 dated Jul. 17, 2014.
Extended European Search Report for Application No. 15000033.9 dated Jun. 24, 2015.
"Non-Toxic and Bio-Compatible Type 2 Titanium Anodizing", 2003, XP055117504, Retrieved from the Internet: <URL: http://www.danco.net/PDF-DOWNLOADS/TITANIUM I I.pdf>, [retrieved on May 12, 2014].

(56) References Cited

OTHER PUBLICATIONS

Aberg et al, Bisphosphonate incorporation in surgical implant coatings by fast loading and co-precipitation at low drug concentrations, J Mater Sci: Mater Med (2009) 20:2053-2061.
Abtahl et al, A bisphosphonate-coating improves the fixation of metal implants in human bone, A randomized trial of dental implants, Bone 50 (2012) 1148-1151.
Brohede et al, Multifunctional implant coatings providing possibilities for fast antibiotics loading with subsequent slow release, J Mater Sci: Mater Med (2009) 20:1859-1867.
Brunski et al, Biomaterials and Biomechanics of Oral and Maxillofacial Implants: Current Status and Future Developments, The Inrternational Journal of Oral & Maxillofacial Implants, 2000. 15-46.
F. Chai et al, Antibacterial activation of hydroxyapatite (HA) with controlled porosity by different antibiotics, Biomolecular Engineering 24 (2007) 510-514.
Forsgren et al, Co-loading of bisphosphonates and antibiotics to a biomimetic hydroxyapatite coating, Biotechnol Lett (2011) 33:1265-1268.
Hetrick et al, Reducing implant-related infections: active release strategies, I Chem. Soc. Rev., 2006, 35, 780-789.
Hutson et al, Infections in Periarticular Fractures of the Lower Extremity Treated with Tensioned Wire Hybrid Fixators, Journal of Orthopaedic Trauma vol. 12, No. 3, 1998, pp. 214-218.
International Search Report for Application No. PCT/EP2013/068082 dated May 26, 2014.
International Search Report for Application No. PCT/IB2014/060905 dated Jun. 26, 2014.
International Search Report for Application No. PCT/IB2014/062454 dated Sep. 29, 2014.
James M Anderson, Biological Responses to Materials, Annu. Rev. Mater. Res. 2001. 31:81-110.
Johan Forsgren et al, Formation and adhesion of biomimetic hydroxyapatite deposited on titanium substrates, Acta Biomaterialia 3 (2007) 980-984.
K.C. Baker et al, Growth, characterization and biocompatibility of bone-like calcium phosphate layers biomimetically deposited on metallic substrata, Materials Science and Engineering C 26 (2006) 1351-1360.
Lilja et al, Photocatalytic and antimicrobial properties of surgical implant coatings of titanium dioxide deposited though cathodic arc evaporation, Biotechnol Lett (2012) 34:2299-2305.
Liu et al, Water-based sol-gel synthesis ofhydroxyapatite: process development, Biomaterials 22 (2001) 1721-1730.

M.P. Ginebra et al, Calcium phosphate cements as bone drug delivery systems: A review, Journal of Controlled Release 113 (2006) 102-110.
Ma et al, Electrophoretic deposition of porous hydroxyapatite scaffold, Biomaterials 24 (2003) 3505-3510.
Mahan et al, Factors in Pin Tract Infections, Department of Orthopedic Surgery, University of Louisville, Louisville, Ky., Mar. 1991 vol. 14 No. 3 V , pp. 305-308.
Masse et al, Prevention of Pin Track Infection in External Fixation with Silver Coated Pins: Clinical and Microbiological Results, J Biomed Mater Res (Appl Biomater) 53: 600-604, 2000.
Poelstra et al, Prophylactic treatment of gram-positive and gram-negative abdominal implant infections using locally delivered polyclonal antibodies, pp. 206-215.
Sergio Allegrini Jr., et al, Hydroxyapatite grafting promotes new bone formation and osseointegration of smooth titanium implants, Ann Anat 188 (2006) 143-151.
Stigter M et al: "Incorporation of different antibiotics into carbonated hydroxyapatite coatings on titanium implants. release and antibiotic efficacy", Journal of Controlled Release, Elsevier, Amsterdam, NL, vol. 99, No. 1, Sep. 14, 2004 (Sep. 14, 2004). pp. 127-137, XP004549075.
Stigter M et al: "Incorporation of tobramycin into biomimetic hydroxyapatite coating on titanium", Biomaterials. Elsevier Science Publishers BV, Barking, GB, vol. 23, No. 20, Oct. 1, 2002 (Oct. 1, 2002), pp. 4143-4153. XP004370405.
Synthes CMF, "Modular Sternal Cable System", 2006, 12 pages.
Synthes CMF, "Sternal ZipFix System—For fast and stable fixation of the sternum", Technique Guide, 2011, 26 pages.
Sörensen et al., "Biomechanical and antibacterial properties of Tobramycin loaded hydroxyapatite coated fixation pins", Journal of Biomedical Materials Research B: Applied Biomaterials, 2014, vol. 00B, Issue 00, 12 pages.
Sörensen et al., "Biomimetic Hydroxyapatite Coated Titanium Screws Demonstrate Rapid Implant Stabilization and Safe Removal In-Vivo", Journal of Biomaterials and Nanobiotechnology, 2015, 6, 20-35.
Tengvalla et al, Surface immobilized bisphosphonate improves stainless-steel screw fixation in rats, Biomaterials 25 (2004) 2133-2138.
Ulrika Brohede et al: "Multifunctional implant coatings providing possibilities for fast antibiotics loading with subsequent slow release", Journal of Materials Science: Materials in Medicine, Kluwer Academic Publishers, BO, vol. 20, No. 9, 28 Apr. 1, 2009 (Apr. 28, 2009) pp. 1859-1867, XP019730963.
Zilberman et al, Antibiotic-eluting medical devices for various applications, journal of Controlled Release 130 (2008) 202-215.

* cited by examiner

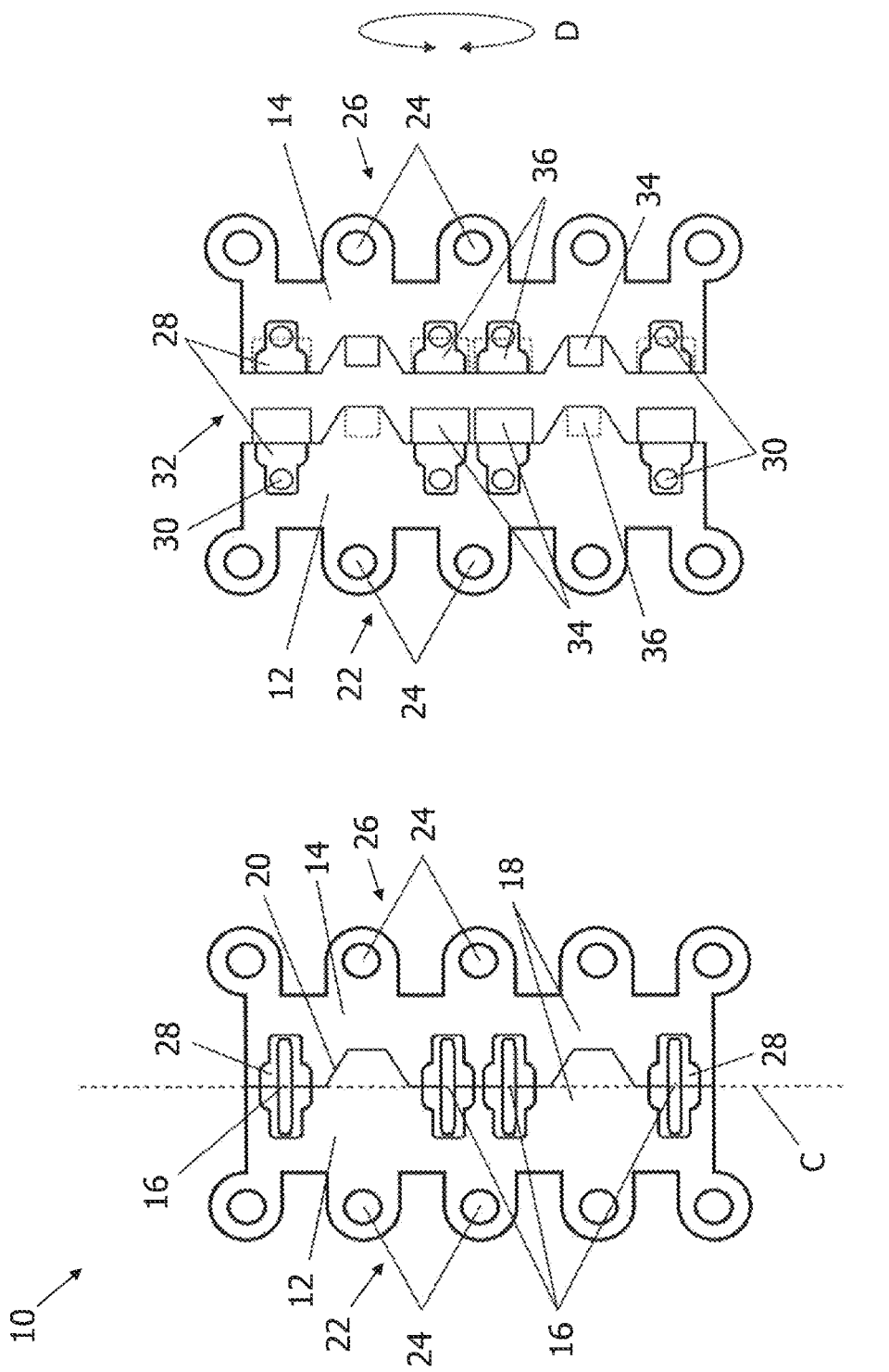

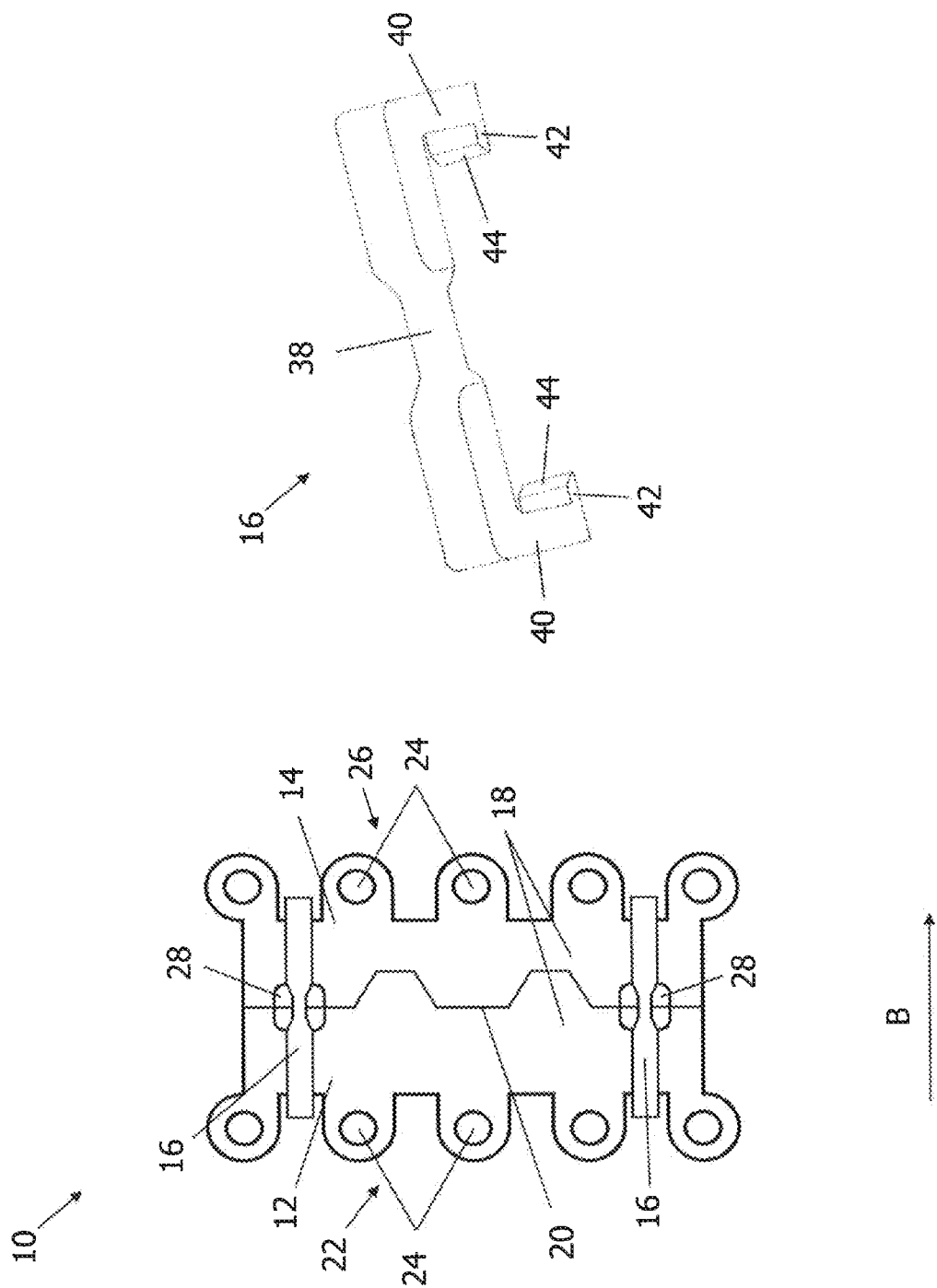

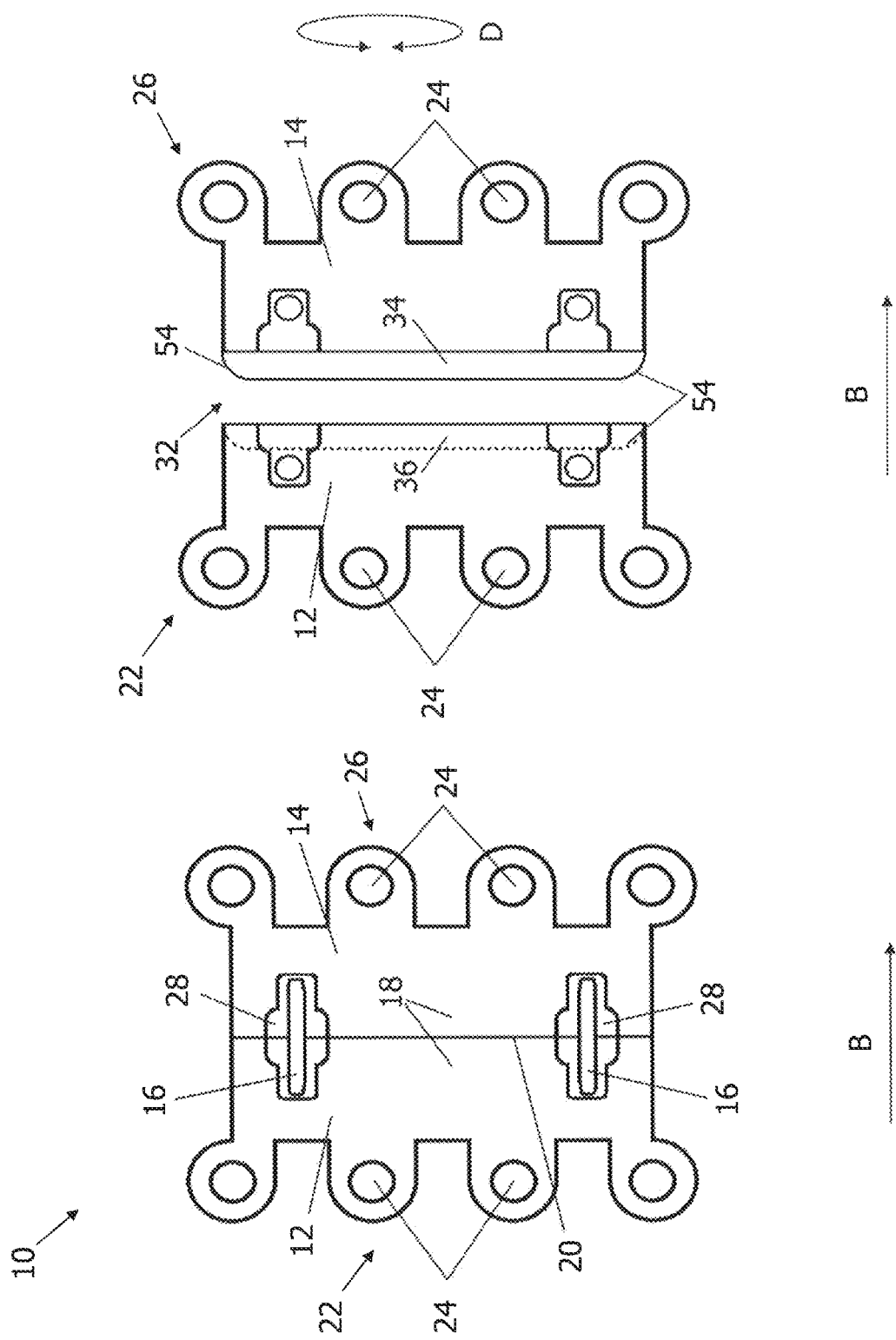

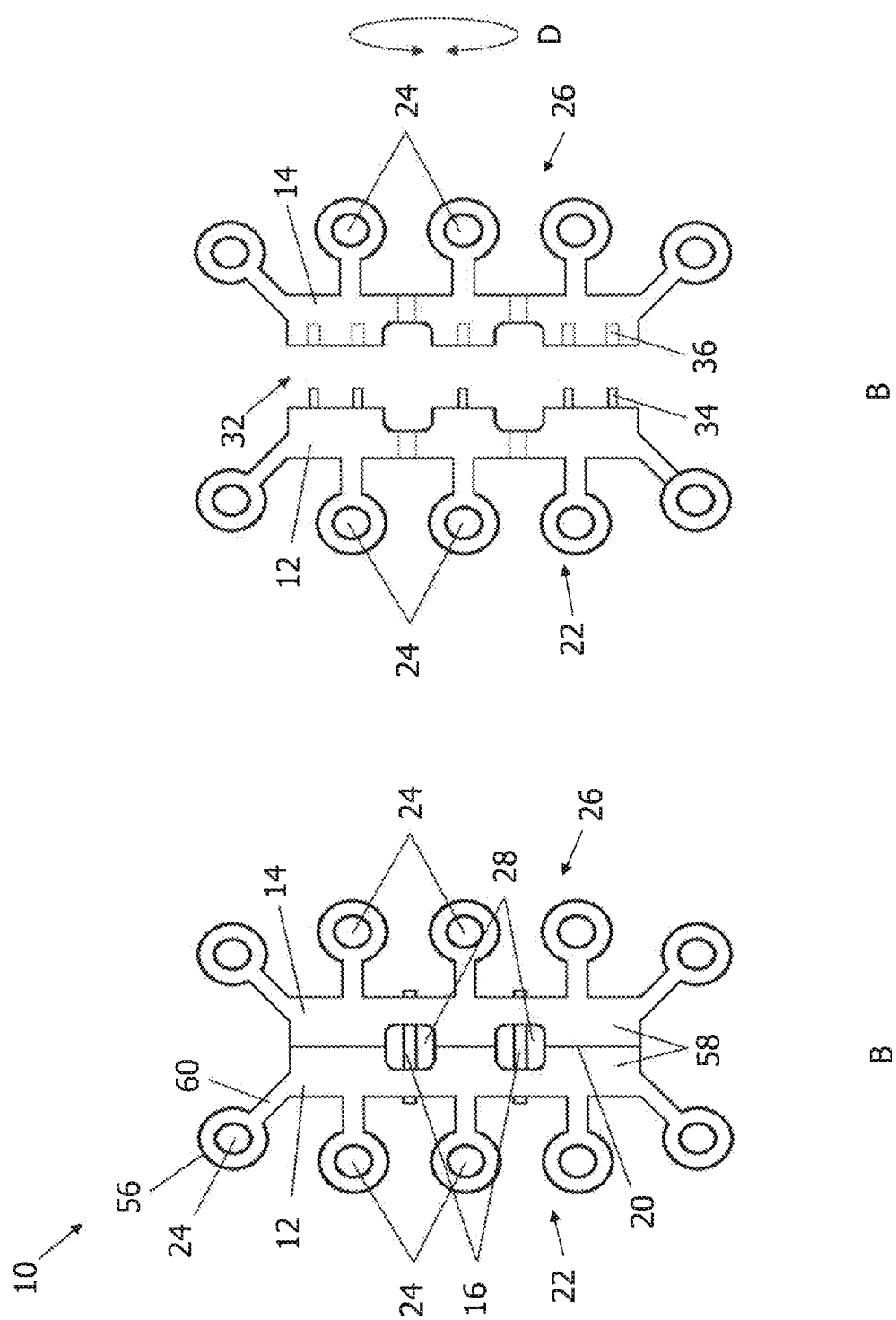

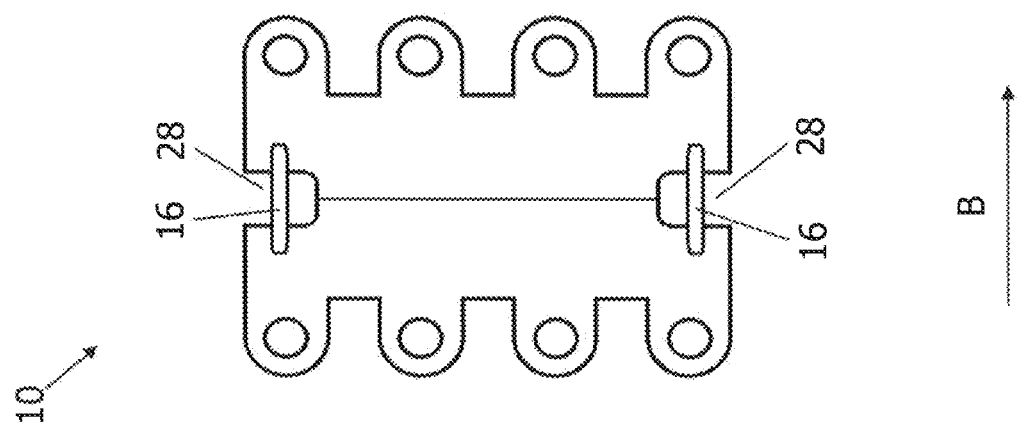
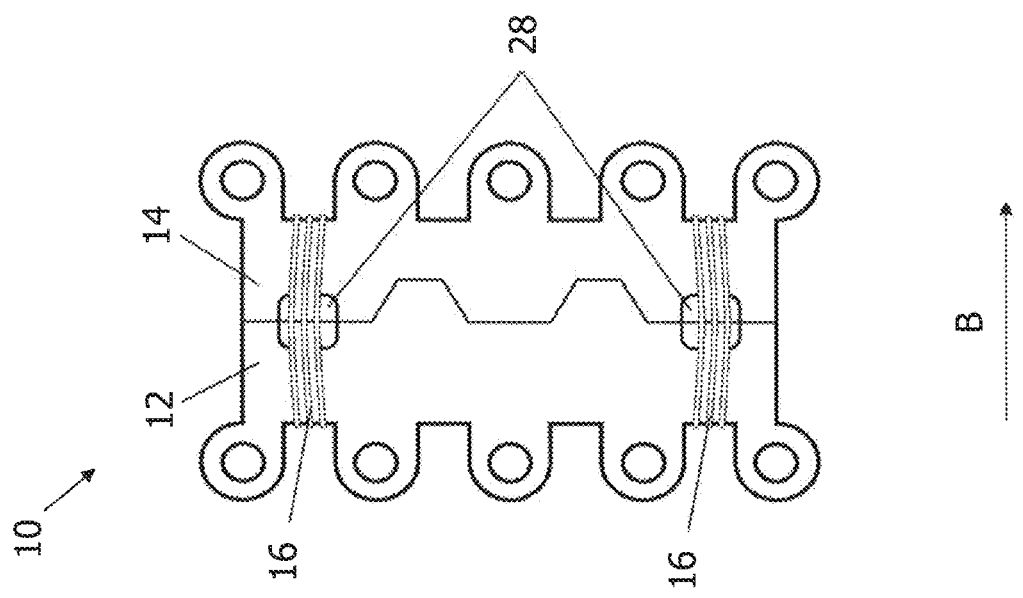
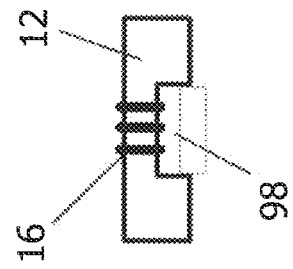

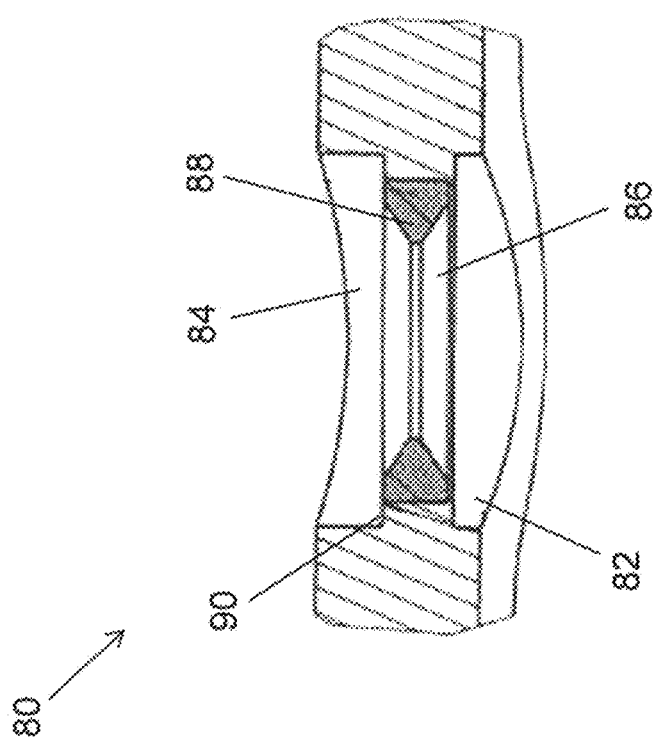

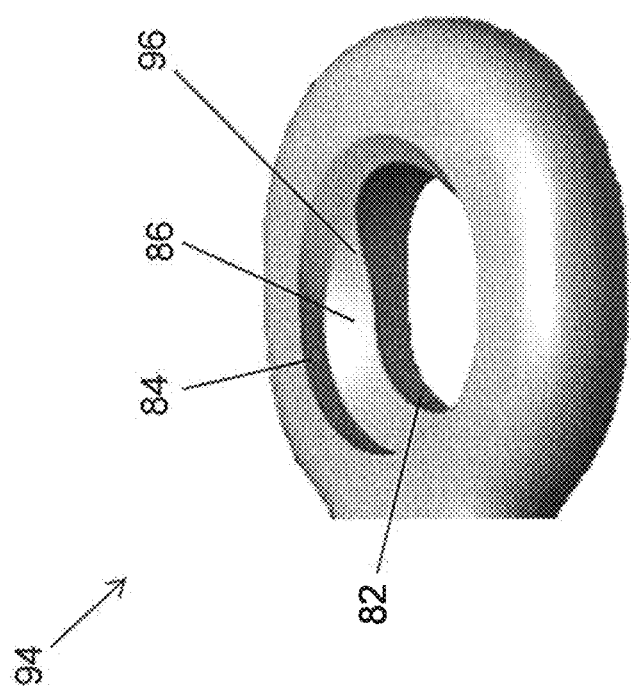

FIXATION ASSEMBLY WITH MULTIPLE SECTIONS FOR SECURING PARTS OF A STERNUM

CROSS-REFERENCE TO RELATED APPLICATIONS

The present application claims the benefit of European Patent Application No. 13003896.1 filed Aug. 5, 2013 and U.S. Provisional Patent Application No. 61/845,024 filed Jul. 11, 2013, the disclosures of which are incorporated herein by reference.

BACKGROUND OF THE INVENTION

The present disclosure generally relates to sternal fixation. Specifically, the disclosure relates to a fixation assembly for securing parts of a sternum and to a system comprising the fixation assembly.

Various surgical procedures require the surgeon to access the thoracic region of a patient. A known procedure to access the thoracic region is to cut the sternum in two parts and separate these two parts from each other. After completion of the surgical procedure, the separated parts of the sternum are brought back to their initial position and fixed, for example, with a bone plate attached to the sternum parts or a wire tensioned around the circumference of the sternum.

EP 1365693 B1 (U.S. Pat. No. 6,872,210) relates to a sternal fixation device comprising two mating plates and a release member. The two plates are held together by the release member, and by removing the release member, the two plates can be separated.

US 2006/116683 A1 relates to a fixation assembly comprising a contoured plate and a securing plate. The contoured plate may have a plurality of teeth and the securing plate may have a resilient securing member.

After a surgical procedure such as, for example, a bypass operation has been carried out on a patient and the sternum has been closed using any of the known fixation assemblies, the patient is normally kept under surveillance. If it is detected that the surgical procedure has failed in any manner, it may be desirable for the surgeon to again open the sternum closure. The time required for this sternum opening procedure may be critical for the patient's health and even life.

BRIEF SUMMARY OF THE INVENTION

There is a need for a fixation assembly for securing parts of a sternum that can be separated fast, easily and at low risk for the patient. Furthermore, there is a need for a fixation assembly for securing parts of a sternum that exhibits good surgical results.

According to one aspect, a fixation assembly for securing parts of a sternum is provided, wherein the assembly comprises a first section having a first attachment structure for securing the first section to a first sternum part, a second section having a second attachment structure for securing the second section to a second sternum part, a mating arrangement defining a mating direction and a predetermined relative position between the first and second sections in a plane perpendicular to the mating direction, and at least one holding member for detachably holding the first and second sections in an abutting relationship in the predetermined relative position.

At least one of the first section and the second section may be constituted by a bone plate. One or both of the first and second sections may have a flat appearance. The thickness of the first and second sections may be between 1.5 and 6 mm, for example 2 to 3 mm (e.g., approximately 2.5 mm). The fixation assembly may have a length between 10 and 80 mm (e.g., between 25 and 55 mm).

Furthermore, at least one of the first and second sections may be made of a plastic material, for example polyetheretherketone (PEEK). Alternatively, at least one of the first and second sections may be made of metal. The first section or the second section, or both, may be injection molded. The first section and the second section may be made of a biocompatible material, for example, a biocompatible metal such as titanium, an alloy of titanium or stainless steel.

At least one of the first and second sections may be flexible. This flexibility may allow the fixation assembly to flex about at least one axis in its extension plane. Alternatively, or in addition, the lower surface of the fixation assembly may have a profile that matingly conforms with the sternum. This profile may have a concave appearance. Furthermore, this profile may be made generic or patient specific, for example by adapting the shape of the profile based on a computed tomography (CT) scan of the sternum of a patient.

The mating arrangement may be disposed on respective mating faces of the first and second sections. In one variant the mating arrangement is an integral part of the first and second sections. The mating arrangement and the at least one holding member may be different structures.

The at least one holding member may detachably hold the first and second sections in an abutting relationship in the predetermined relative position by simultaneous engagement of the first and second sections substantially along the mating direction. A direction substantially along the mating direction may be referred to as a direction angled less than 25 degrees (e.g., less than 15 degrees) with respect to the mating direction.

The at least one holding member may be constituted by one or more elongated flexible members such as a cable or wire. Each elongated flexible member may engage a laterally outer surface of the first and second sections.

The fixation assembly may further comprise at least one receiving structure configured to receive the at least one holding member or a section thereof. The at least one receiving structure may be provided in the first section or the second section. Alternatively, the at least one receiving structure may be jointly constituted by the first and second sections. The at least one receiving structure can be arranged on a bone contacting side of the fixation assembly. Moreover, the at least one receiving structure may be formed as a recess, an opening or a groove. The receiving structure may substantially be O-, U- or V-shaped in cross-section.

The at least one receiving structure may extend substantially along the mating direction or substantially perpendicular thereto. Thus, the receiving structure may extend substantially in a direction of a longitudinal axis of the fixation assembly or substantially perpendicular thereto. Thus, the at least one receiving structure may extend substantially perpendicular to the extension plane of the first and second sections when in the predetermined relative position.

Further, the at least one receiving structure may be arranged at a central portion or at an outer portion (e.g., an end portion) of the fixation assembly. The receiving structure may be configured to receive a surgical cable or wire (e.g., a Kirschner wire, K-wire) or another flexible member. Alternatively, or in addition, the at least one receiving structure may be configured to receive a further fixation assembly including a flexible elongated member. The further fixation assembly may be formed as a zip tie.

The fixation assembly may be configured to maintain the abutting relationship (e.g., to establish the simultaneous engagement) by engaging two substantially oppositely facing surfaces with the at least one holding member. The oppositely facing surfaces may be laterally offset relative to the mating direction. This engagement may be realized by providing a hole, protrusion or other structure in or on each of the first and second sections and a holding member engaging these two structures. Such holding member may be constituted by a staple. The staple may be substantially U-shaped. Each end of the staple may be received in holes or a similar structure, and a bridging portion of the staple may bridge the junction between the first and second section.

Alternatively, or in addition, the two substantially oppositely facing surfaces may be constituted by laterally outer surfaces of the first and the second sections, respectively. In this realization, a holding member in the form of a clip may be used. The clip may for example be made of a metal such as titanium, an alloy thereof or a shape-memory material such as, for example, NiTiNol which is a metal alloy of nickel and titanium.

As a further possible realization, the two substantially oppositely facing surfaces may be constituted by a locking profile extending substantially perpendicular to the mating direction. The locking profile may be jointly constituted by the first and second sections. According to one configuration, the locking profile has a substantially cylindrical appearance of any cross-sectional shape. A plurality of locking profiles and holding members engaging the locking profiles in the predetermined position may be provided in the fixation assembly.

The fixation assembly may be configured to have the at least one holding member cut open by a surgical tool. In other words, this configuration enables a cutting edge or blade to move (e.g., in a direction substantially perpendicular to the mating direction) without interfering with the first section or the second section when cutting the holding member. The surgical tool may be a cutting device such as a plier.

The fixation assembly may further comprise at least one depression or aperture associated with the at least one holding member for facilitating access by the surgical tool to cut the at least one holding member when holding the first and second sections in the predetermined relative position. The aperture may be provided in the first section or the second section. Alternatively, the aperture may be jointly constituted by the first and second sections. The aperture may be circumferentially closed in one plane. The aperture may be a blind hole or a through hole, for example an opening extending through at least one of the first and second sections in a normal direction with respect to the sternum. A normal direction with respect to the sternum is referred to as a direction substantially perpendicular to the mating direction and substantially perpendicular to the extension plane of the first and second sections when in the predetermined relative position.

The aperture may be used by a surgeon to register the fixation assembly during installation on the sternum. The aperture may be formed (or used) as a window for aligning the fixation assembly correctly on the sternum by allowing a surgeon to view through the aperture. Thus, a sternotomic cut between the two sternum parts can be detected through the aperture such that the fixation assembly may then be positionally oriented on the two sternum parts. A surgeon can thus exactly align the fixation assembly on the sternum by viewing through this aperture.

The fixation assembly may be configured to establish the holding of the first and second sections by the at least one holding member by a snap fit. This may be accomplished with a holding member having elasticity in at least one direction. For example, such holding member may be constituted by a flexible ring. Alternatively, a flexible clip may be pushed into engagement with the oppositely facing laterally outer surfaces of the first and second sections by a snap fit. Such clip may have two hooks substantially corresponding to the outer contours of these laterally outer surfaces.

The at least one holding member may comprise a shape-memory material and have an original shape for disengagement of the holding of the first and second sections by the holding member. This shape-memory material may be nickel titanium (i.e., a metal alloy of nickel and titanium), also known as NiTiNol. The original shape is referred to as the "undeformed" shape that the holding member adapts when heated above its transformation temperature or when cooled below its transformation temperature. According to one realization, such holding member may be a ring having a first diameter and when cooled to a temperature below its transformation temperature, the ring adapts a second diameter, larger than the first diameter.

The mating arrangement may comprise at least one protrusion arranged on one of the first and second sections and at least one recess configured to accommodate the at least one protrusion, arranged in the other one of the first and second sections. Both the at least one protrusion and the at least one recess may be substantially centrally disposed in the thickness direction of the first and second sections. The thickness direction is referred to as the normal direction with respect to the extension plane of the fixation assembly.

The at least one protrusion may have a cross-shape or X-shape. Alternatively, or in addition, the at least one protrusion may be a lip extending substantially perpendicular to the mating direction. Moreover, the lip may extend substantially parallel with the extension direction of the first and second sections when in the predetermined relative position.

The mating arrangement may comprise a plurality of pairs of protrusions and corresponding recesses. The protrusions may be pins. The recesses may be holes with a circumferential profile substantially corresponding to the pins. For example, each of the first and second sections may comprise both a protrusion and a recess. As a further realization, the protrusions may be tabs each having a substantially flat appearance. The tabs may also be referred to as lips.

Furthermore, the mating arrangement may comprise a plurality of pairs of protrusions and recesses disposed in different planes parallel with the extension plane of the fixation assembly. For example, at least one first pair of protrusion and recess may be disposed in a first plane and at least one second pair of protrusion and recess may be disposed in a second plane. Both the first and second planes may substantially be parallel with the extension plane of the fixation assembly.

At least one third pair of protrusion and recess may be disposed in a third plane. In this realization, the configuration of protrusions and recesses in the first and third planes may be the same while the configuration of the at least one pair of protrusion and recess in the second plane may be mirrored, in a plane substantially perpendicular to the mating direction, with respect to the configuration in the first and third planes.

The abutting relationship between the first and second sections may be defined by an abutment of at least one protrusion with at least one recess along the mating direction. Alternatively, or in addition, the abutting relationship between the first and second sections may be defined by mating faces, provided on each of the first and second sections. The mating faces may extend in a plane substantially perpendicular with the mating direction when the first and second sections are in the predetermined relative position.

The first and second sections may be configured to abut against each other along a straight, zig-zag-shaped or ondulating junction in the predetermined relative position. This junction may generally be referred to as a mating line. A zig-zag junction may comprise at least two straight portions that are connected at an apex. The junction may generally be flush with an exterior surface of the fixation assembly in the predetermined relative position.

For example, the zig-zag junction may be provided in the upper surface of the fixation assembly. The upper surface of the fixation assembly is referred to as the opposite surface with respect to the surface applied to the sternum. That is, the upper surface may be a side opposite a bone contacting side of the fixation assembly. Alternatively, or in addition, the zig-zag junction may be provided in the lower surface of the fixation assembly. The lower surface may be a bone contacting side of the fixation assembly.

The at least one holding member may have an opening, wherein inner surfaces of the opening are configured to establish the holding of the first and second sections. This opening of the holding member may have a circular appearance. One such holding member is a ring. Alternatively, the holding member may have a triangular, square or pentagonal opening. The holding member may be rigid or flexible.

Each of the first and second sections may comprise at least one opening extending substantially perpendicular to the mating direction for receiving a part of the at least one holding member. Such opening may be a blind opening and/or a through opening. For example, the ends of a staple may be secured in these openings. The staples may be glued, welded or otherwise secured to the openings.

The first and/or the second attachment structure may comprise at least one opening for receiving a bone fastener. The at least one opening may have a conical, convex or spherical taper which substantially tapers inwardly in a direction toward a bone contacting surface of the first and second section respectively. The taper may be formed as a countersink. Thus, at least one opening can be configured to exert a force on the opposite section when a bone fastener is screwed or inserted through the at least one opening to the sternum.

In one implementation, the at least one opening of the first or second section may have an inclined surface onto which a bone fastener is able to slide in a fastening or compression position. The at least one opening may permit a bone fastener to slide laterally or longitudinally with respect to the opening or the first and second section, respectively. Further, the at least one opening may define a predetermined direction for a bone fastener. The inclined surface may have a predetermined angle with respect to an extension plane of the first or second section. The predetermined angle may be between about 20 and 70 degrees, for example about 40 to 50 degrees (e.g., about 45 degrees) with respect to the extension plane of the first and second sections when in the predetermined relative position.

The at least one opening of the first or second section may be a circular or elongated hole. The elongated hole may be an oblong hole. Further, the elongated hole may extend substantially parallel with respect to the mating direction. Alternatively, the elongated hole may extend substantially perpendicular to the mating direction. The elongated hole may permit a bone fastener to slide laterally with respect to the elongated hole.

In one realization, the at least one opening of the first or second section may include a locking feature configured to lock a bone fastener to the first or second section. The locking feature may include a threaded portion or one or more lips in a circumferential direction adapted to engage a bone fastener (e.g., a threaded head thereof). Further, the locking feature may engage a threaded head of a bone fastener at a selected angular orientation. The at least one opening of the first or second section may have a multiple thread (e.g., a double thread). Further, the at least one opening of the first or second section may comprise a threaded portion on a bone contacting side of the first or second section and an unthreaded portion on a side opposite to the bone contacting side thereof.

Each of the first and second section may include multiple openings for receiving bone fasteners. The first or second section may have an opening for receiving a bone fastener substantially perpendicular to bone. In one implementation, the first or second section may include a hole for receiving a bone fastener substantially perpendicular to bone and arranged substantially aligned with an oblong hole along the mating direction or, alternatively, perpendicular thereto. Alternatively, or in addition, a hole having a locking feature for engaging a threaded head of the bone fastener at a selected angular orientation may be arranged on the first or second section substantially aligned with an elongated hole along the mating direction or, alternatively, perpendicular thereto.

The first and second sections may each comprise an alternate arrangement of holes (locking holes) having a locking feature for locking a bone fastener to the frist or second section and elongated (or oblong) holes. Further, the first and second sections may each comprise an alternate arrangement of circular holes and elongated or oblong holes. For example, the first, third and fifth holes of the first section and the second and fourth holes of the second section may be elongated holes and/or the second and fourth holes of the first section and the first, third and fifth holes of the second section may be holes having a locking feature for locking a bone fastener to the first or second section. Alternatively, or in addition, the locking holes may receive a bone fastener substantially perpendicular to bone.

The at least one opening of the first or second section may have a central axis which is oblique relative a vertical axis of the first or second section, e.g. of an extension plane thereof. An angle defined between the central axis and the vertical axis can be approximately between 0° and 60°. Alternatively, the at least one opening of the first or second section may be oblique relative to an upper surface (e.g., a side opposite a bone contacting side) or lower surface (e.g., a bone contacting side) of the first or second section.

Furthermore, a system is provided comprising a fixation assembly as generally described above and hereinafter and at least one bone fastener. The at least one bone fastener may be a locking screw, a cortical screw, a compression screw or bone peg. The at least one bone fastener may be a bone screw with a threaded head for (e.g., monoaxial or polyaxial) engagement of the locking feature at a desired angle. The system may further comprise a surgical tool for cutting the at least one holding member.

BRIEF DESCRIPTION OF THE DRAWINGS

Further details, advantages and aspects of the present disclosure will become apparent from the following embodiments taken in conjunction with the drawings, wherein:

FIG. 1 shows a fixation assembly according to a first embodiment in a connected configuration;

FIG. 2 shows a first and second section according to the first embodiment in a separated configuration;

FIG. 3 shows a fixation assembly according to a second embodiment in a connected configuration;

FIG. 4 shows a holding member according to the second embodiment;

FIG. 8 shows a fixation assembly according to a fourth embodiment in a connected configuration;

FIG. 9 shows the first and second sections according to the fourth embodiment in a separated configuration;

FIG. 10 shows a fixation assembly according to a fifth embodiment in a connected configuration;

FIG. 11 shows the first and second sections of the fifth embodiment in a separated configuration;

FIG. 14 shows a fixation assembly according to an eighth embodiment in a connected configuration;

FIG. 15A shows a fixation assembly according to a ninth embodiment in a connected configuration;

FIG. 15B shows a detailed cross-sectional view of the fixation assembly according to the ninth embodiment shown in FIG. 15A;

FIG. 19 is a cross-sectional view of an alternative locking screw hole embodiment;

FIG. 21 is a perspective view of an alternative hole embodiment.

DETAILED DESCRIPTION

Figure 6:
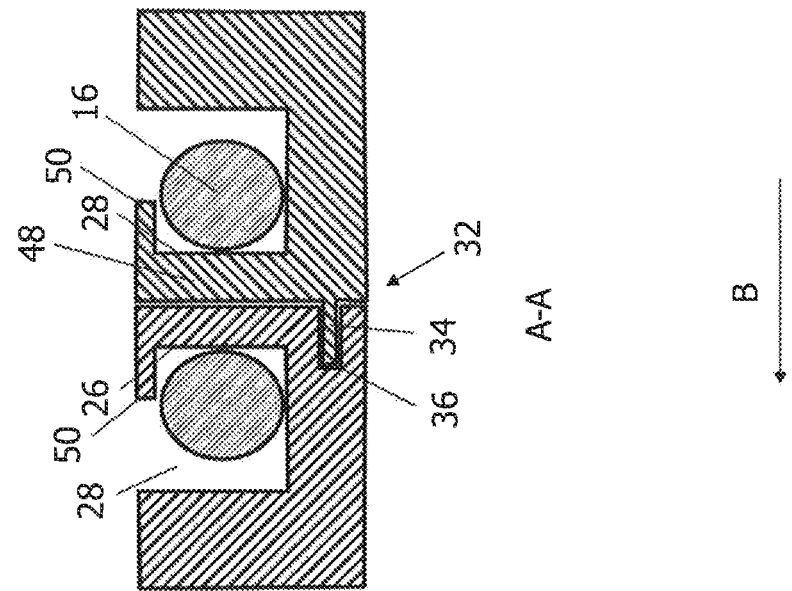
FIG. 6 shows a cross-sectional view of line A-A in FIG. 5.

In the following, embodiments of a fixation assembly for securing parts of a sternum will be described. The same reference numerals will be used to denote the same or similar structural features. A "closed configuration" of the first and second sections and a "predetermined relative position" between the first and second sections are used to denote the same positional relationships between the first and second sections.

FIG. 1 shows a fixation assembly 10 according to a first embodiment in a connected configuration. The fixation assembly 10 comprises a first section 12, a second section 14 and a plurality of holding members 16. Here, four holding members 16 are depicted.

The first and second sections 12, 14 have a substantially flat appearance. That is, the first and second sections 12, 14 extend substantially in the plane of FIG. 1. The upper surfaces of the first and second sections 12, 14 mate or abut along a junction 20.

As can be seen in FIG. 1, the junction 20 has a zig-zag configuration in the present embodiment. That is, the junction 20 comprises a plurality of straight portions that are connected at an apex. The junction 20 is flush with the upper surfaces 18 of the first and second sections 12, 14. Thus, the zig-zag configuration of the junction 20 defines protrusions and recesses also in the upper surfaces 18 of the first and second sections 12, 14. This configuration may additionally be provided at the lower surfaces of the first and second sections 12, 14, i.e., the surfaces facing the sternum when the fixation assembly 10 is attached to a sternum. In this manner, pairs of protrusions 34 and recesses 36 can be disposed in three different planes parallel with the extension plane of the fixation assembly 10.

The first section 12 comprises an attachment structure 22 having a plurality of openings in form of screw holes 24. Here, five screw holes 24 are employed. These screw holes 24 are substantially aligned. Similarly, the second section 14 comprises an attachment structure 26 comprising a plurality of openings in form of screw holes 24. The attachment structure 26 of the second section 14 also comprises five screw holes 24.

The screw holes 24 may be threaded or unthreaded. The screw holes 24 each serve to receive a bone fastener for securing the first and second sections 12, 14 to the sternum. The bone fasteners may be bone screws. The screw holes 24 may be countersunk and comprise a locking feature for engaging a threaded head of the bone fastener at a selected angular orientation.

In the present embodiment, each of the screw holes 24 includes a locking feature. The locking feature is configured to lock a bone fastener (not shown in FIG. 1) to the first or second section 12, 14. The locking feature includes a threaded portion. In the present embodiment, the locking feature of the screw holes 24 is formed as a thread, e.g., a threaded hole portion. Alternatively, or in addition, the locking feature may be formed as one or more circumferential lips, as a bayonet-type feature or otherwise. The threaded portion of the locking feature is adapted to engage a bone fastener, e.g., engage a threaded head of a bone fastener. Thus, each of the screw holes 24 can have a circumferential thread or is partially threaded.

In the present embodiment, the screw holes 24 are formed as circular holes. Each of the screw holes 24 may have a conical taper which substantially tapers inwardly in a direction towards a bone contacting surface of the first or second section 12, 14 in a conical fashion. Alternatively, the at least one of the screw holes 24 may have a convex or spherical taper, i.e., has a curved shape. The taper may form a countersink.

A cone angle of the taper of a screw hole 24 may generally be between 1 degree and 80 degrees, and is approximately 45 degrees in the present embodiment. Thus, a screw hole 24 may be, on the one hand, adapted to slidingly receive bone fasteners (such as sliding or compression screws), and, on the other hand, adapted to receive a locking screw or a cortical screw. In case of a locking screw, a threaded head thereof mates with the locking feature of the screw hole 24 for providing an angularly stable locking engagement therebetween at a pre-defined angle (i.e., monoaxially).

Each of the holding members 16 is directed substantially in a mating direction B. The mating direction B refers to a direction in which the first and second sections 12, 14 are brought together into the illustrated connected configuration.

As can be seen in FIG. 1, each of the holding members 16 bridges the junction 20. Furthermore, each of the holding members 16 is engaged with the first and second sections 12, 14, respectively.

In this embodiment, the holding members 16 are constituted by staples. The staples 16 may be made of metal, for example NiTiNol or titanium. Each staple 16 is engaged with an opening (hidden in FIG. 1) in each of the first and second sections 12, 14. Thus, each staple 16 is simultaneously engaging the first and second sections 12, 14 along the mating direction B. Thereby, each of the holding members 16 prevents the first and second sections 12, 14 from relative displacement along the mating direction B.

Furthermore, in FIG. 1, the first and second sections 12, 14 are mated in a predetermined relative position in a plane C perpendicular to the mating direction B. Thus, the plane C is perpendicular to the extension plane of the fixation assembly 10.

The fixation assembly 10 comprises four apertures 28, with one aperture 28 associated with each of the holding members 16. In this realization, the apertures 28 are jointly constituted by the first and second sections 12, 14. The upper surfaces 18 of the first and second sections 12, 14 are substantially aligned in one plane in the connected configuration. Also the holding members 16 are substantially aligned with the upper surfaces 18. The apertures 28 are apertures with respect to the upper surfaces 18. In this way, a surgical tool can partially be inserted into each aperture 28 at opposite positions with respect to the holding member 16 and the holding member 16 can then be cut open by the surgical tool. Moreover, the aperture 28 is configured as a window to permit a surgeon to register the fixation assembly 10 relative to a sternotomical cut on which the fixation assembly 10 has to be centrally positioned. It will be appreciated that in other embodiments additional or alternative windows would be provided (i.e., independently from any holding member 16).

In the present embodiment, the holding members 16 in the form of staples are fixed to the openings of the first and second sections 12, 14, for example by welding or otherwise. When the holding members 16 are cut open, the first and second sections 12, 14 can be separated from each other along the mating direction B. During this separation, the cut parts of the holding members 16 remain fixed to the openings of the first and second sections 12, 14. Thus, no loose parts of the holding members 16 risk to fall into a surgical site when separating the fixation assembly 10.

FIG. 2 shows the first and second sections 12, 14 in a separated configuration. The holding members 16 are not depicted in this drawing. In FIG. 2, the plurality of openings for receiving the holding members 16 can be seen. The openings 30 are blind openings (i.e., they do not extend fully through the first and second sections 12, 14).

In FIG. 2, a mating arrangement 32 can also be seen. The first and second sections 12, 14 comprise a plurality of protrusions 34 and a plurality of corresponding recesses 36 which constitute the mating arrangement 32. The protrusions 34 are here realized as tabs (i.e., they have a substantially flat appearance). Each tab is therefore forming a lip. Additionally, the tabs 34 are substantially aligned with the extension plane of the first and second sections 12, 14, respectively. The extension plane of the first and second sections 12, 14 is referred to as the plane of the drawings in FIGS. 1 and 2. The tabs 34 may be formed as integral parts of the first and second sections 12, 14, for example through injection molding. Thus, the mating arrangement 32 is configured to rotationally lock the first and second sections 12, 14 relative to each other in the predetermined relative position against rotation about an axis substantially parallel with the mating direction B.

As can be seen in FIG. 2, each pair of openings 30 is substantially aligned along the mating direction B. The surfaces of each pair of openings 30 facing the mating arrangement 32 constitute substantially oppositely facing surfaces. As can further be gathered from FIG. 2, when the first and second sections 12, 14 are brought together along the mating direction B into the connected configuration (as illustrated in FIG. 1), the protrusions 34 engage with the recesses 36, and relative rotation between the first and second sections 12, 14 in the direction D is thereby prevented. In other words, the mating arrangement 32 rotationally locks the first and second sections 12, 14 relative to each other in a predetermined relative position against rotation about an axis substantially parallel with the mating direction B.

As one possible modification, instead of welding the staples 16 to the openings 30 and cutting the staples 16 open, the properties of a shape-memory material (such as NiTiNol) may be employed for the staple 16. This can be done by configuring at least one of the openings 30 larger than the corresponding end of the staple 16 such that the staple 16 is allowed to expand substantially along the mating direction B while still being received in the openings 30. Thus, the staple 16 may initially engage the opposing surfaces of the openings 30 (i.e., the surfaces closest to the junction 30). When the staple 16 is heated above its transformation temperature or cooled below its transformation temperature, or otherwise activated (e.g., by an electrical current) the engagement of these opposing surfaces is released. In this manner, the staples 16 can be removed from the openings 30 without cutting the staples 16.

FIG. 3 shows a fixation assembly 10 according to a second embodiment in a connected configuration. The mating arrangement 32 in the second embodiment is the same as the mating arrangement 32 in the first embodiment. The fixation assembly 10 in FIG. 3 comprises a first and a second section 12, 14 and a plurality of holding members 16 in the form of clips. Here, two clips 16 are employed.

Each of the clips 16 engages the laterally outer surfaces of the first and second sections 12, 14, respectively. As can be seen in FIG. 3, these laterally outer surfaces are substantially oppositely facing surfaces. Additionally, each of the clips 16 is oriented in the mating direction B. Thus, each clip 16 simultaneously engages the first and second sections 12, 14 substantially along the mating direction B.

The apertures 28 in the second embodiment are slightly modified with respect to the apertures 28 of the first embodiment since no openings 30 are used for fixing the clips 16. In the second embodiment, the apertures 28 are jointly constituted by the first and second sections 12, 14. The apertures 28 are countersunk with respect to the upper surfaces 18.

In this embodiment, the clips 16 are partly disposed above the upper surfaces 18. However, notches in the upper surfaces 18 extending in the mating direction B may be provided for receiving the clips 16 such that the clips 16 are substantially flush with the upper surfaces 18. Alternatively, or in addition, notches may be provided in the laterally outer surfaces of the first and/or second sections 12, 14 for receiving the clips 16 such that the clips 16 are substantially flush with these laterally outer surfaces.

FIG. 4 illustrates a perspective view of the clip 16 in FIG. 3. The clip 16 comprises a narrow portion 38 with a reduced cross-sectional area to be disposed in the region of one of the apertures 28. The narrow portion 38 of the clip 16 facilitates the cutting of the clip 16 by a surgical tool. Furthermore, the narrow portion 38 serves as a visual guidance for applying the surgical tool in an aperture 28.

The clip 16 further comprises two hook portions 40. The hook portions 40 are adapted to engage two substantially oppositely facing surfaces of the first and second sections 12, 14, respectively. The clip 16 may be formed of metal. Furthermore, the clip 16 may be elastic to lock the first and second sections 12, 14 in the connected configuration with a snap fit.

Each hook portion 40 of the clip 16 comprises a lip 42. The lips 42 serve to engage the lower surface of the first and second sections 12, 14, respectively. These lower surfaces are referred to as surfaces facing the sternum when the fixation assembly 10 is connected to the sternum.

As can be seen in FIG. 4, each lip 42 comprises a chamfered edge 44. The chamfered edges 44 facilitate to bias the lips 42 in a direction away from the narrow portion 38 when the hook portions 40 are applied to the laterally outer contours of the first and second sections 12, 14, respectively. The chamfered edges 44 are however optional. When the hook portions 40 are configured to be biased to the outer contours of the laterally outer surfaces of the first and second sections 12, 14, the clip 22 can be cut open without being separated from the first and second sections 12, 14.

As a further possible option, the clip 22 may be made of a shape-memory material (such as NiTiNol) and be released from its engagement of the first and second sections 12, 14 by heating the clip 22 to a temperature above its transformation temperature or by cooling the clip 22 to a temperature below its transformation temperature.

Figure 5:
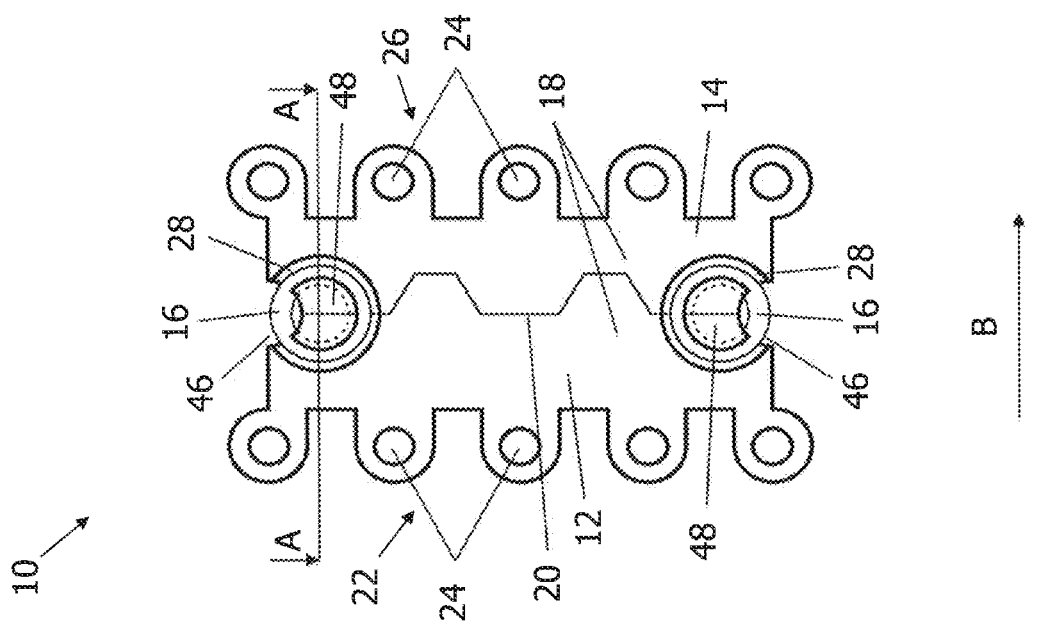
FIG. 5 shows a fixation assembly according to a third embodiment in a connected configuration.

FIG. 5 shows a fixation assembly 10 according to a third embodiment in a connected configuration. The fixation assembly 10 comprises two substantially circular apertures 28. The apertures 28 are countersunk with respect to the upper surfaces 18 of the first and second sections 12, 14. Each aperture 28 is joined with a semi-circular opening 46 extending through the first and second sections 12, 14. In the third embodiment, the semi-circular openings 46 extend in a direction substantially perpendicular to the extension plane of the first and second sections 12, 14.

The fixation assembly 10 further comprises two locking profiles 48 within each of the apertures 28. Each of the locking profiles 48 has a substantially cylindrical appearance. The locking profiles 48 are each jointly constituted by parts of the first and second sections 12, 14. The locking profiles 48 are substantially aligned with the upper surfaces 18.

The holding members 16 of the third embodiment are constituted by rings. In this embodiment, the rings 16 are elastic. Alternatively, these rings 16 may comprise a shape-memory material. The holding members 16 may be attached to the locking profiles (e.g., by welding).

FIG. 6 shows a cross-sectional view along line A-A in FIG. 5. As can be seen in FIG. 6, the locking profile 48 comprises a collar 50. The collar 50 has a slightly larger diameter with respect to the remaining portion of the locking profile 48. The ring 16 circumferentially encloses the locking profile 48 and is prevented by the collar 50 from exiting the aperture 28.

FIG. 6 also illustrates the mating arrangement 32 in the form of a tab 34 extending into a recess 36 and engaging the recess 36. The mating arrangement 32 is the same mating arrangement 32 as described in connection with the first embodiment.

As can be gathered from FIGS. 5 and 6, the rings 16 may be removed from their engagement with the locking profiles by cutting the ring 16 open by a surgical tool in the openings 46. Alternatively, the each ring 16 may be removed from its engagement by grabbing the ring 16 in the opening 46 and pulling the ring 16 away from the locking profile 48 against the elasticity of the ring 16.

In case the ring 16 comprises a shape-memory material, the ring 16 may have a first inner diameter which is smaller than the diameter of the collar 50. The ring 16 may further be configured such that when heated to a temperature above its transformation temperature or when cooled to a temperature below its transformation temperature, the ring 16 adapts a second diameter, larger than the first diameter, and larger than the diameter of the collar 50. The ring 16, when adapting the second larger diameter, can in this state be easily removed from the aperture 28.

It should be noted that a holding member 16 in form of a ring and a corresponding cylindrical locking profile 48 may be replaced with a holding member 16 having polygonal openings (triangular, square etc.) and a locking profile 48 having a cross-section corresponding to the opening of the holding member 16.

Figure 7A:
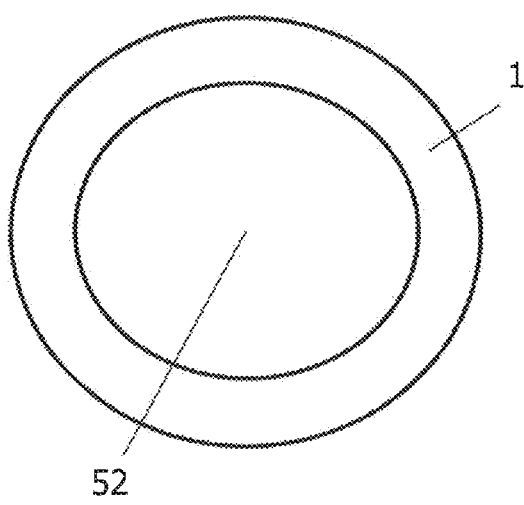
FIGS. 7A-7D show various modifications of holding members.
Figure 7B:
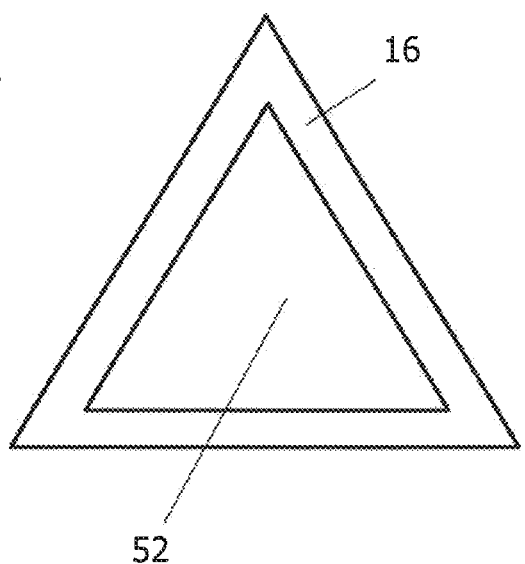
Figure 7C:
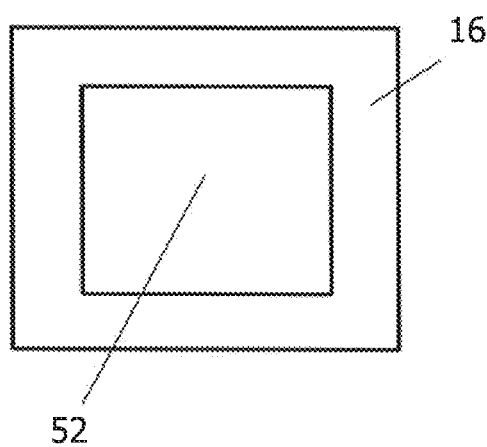
Figure 7D:
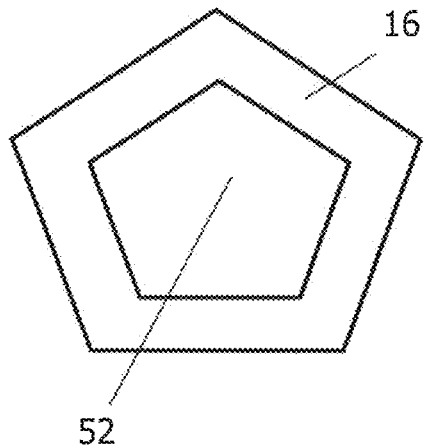

FIGS. 7A to 7D show various modifications of holding members 16 suitable for the third embodiment. FIG. 7A shows a holding member 16 having a circular opening 52. FIG. 7B shows a holding member 16 having a triangular opening 52. FIG. 7C shows a holding member 16 having a square opening 52. FIG. 7D shows a holding member 16 having a pentagonal opening 52. If desired, the cross-section of the locking profile 48 (in the extension plane of the fixation assembly), the apertures 28 and the outer circumferences of the holding member 16 may be adjusted in accordance with the type of opening 52 employed for the holding member 16.

Common for all holding members 16 illustrated in FIGS. 7A to 7D is that each holding member 16 has an opening 52, wherein inner surfaces of the opening 52 are configured to establish a simultaneous engagement of the first and second sections 12, 14 substantially along the mating direction B.

FIG. 8 shows a fixation assembly 10 according to a fourth embodiment in a connected configuration. The holding members 16, the apertures 28 and the openings 30 (not shown) have the same configuration as in the first embodiment. FIG. 8 shows the fixation assembly 10 in a connected configuration. Each of the first and second sections 12, 14 comprises an attachment structure 22, 26 in form of a plurality of openings formed as screw holes 24 aligned along a line. Here, four screw holes 24 are employed. The upper surfaces 18 of the first and second sections 12, 14 abut against each other along a straight junction 20.

FIG. 9 shows the first and second sections 12, 14 according to the fourth embodiment in a separated configuration. As illustrated in FIG. 9, one section, here the second section 14, comprises a protrusion 34 in form of an elongated lip. The lip 34 extends substantially perpendicular to the mating direction B and substantially in the extension plane of the second section 14. The first section 12 comprises a recess 36 in form of a notch for receiving the lip 34. The shape of the notch 36 corresponds to the shape of the lip 34. The lip 34 and notch 36 extend substantially along the entire length of the first and second sections 12, 14, respectively.

Both the notch 36 and the lip 34 comprise rounded edges 54 disposed at their end portions. By engaging the lip 34 with the notch 36, the first and second sections 12, 14 can be brought into a predetermined relative position in a plane perpendicular to the mating direction B. In this position, the first and second sections 12, 14 are rotationally locked against relative movement in direction D (i.e., in a direction about an axis substantially parallel with the mating direction B). The lip 34 may be formed as an integral part of the second section 14, for example through injection molding.

FIG. 10 shows a fixation assembly 10 according to a fifth embodiment in a connected configuration. The attachment structures 22, 26 according to the fifth embodiment have a slightly different structure than the attachment structures 22, 26 of the previous embodiments. The attachment structures 22, 26 each comprises a plurality of rounded members 56 having an opening in form of a screw hole 24.

The rounded members 56 are each connected with main bodies 58 of the first and second sections 12, 14 via a bridge 60. The bridge 60 has a width smaller than the outer diameter of the rounded member 56. In this embodiment, the width of the bridge 60 is also smaller than the diameter of the screw hole 24.

The first and second attachment structures 22, 26 each comprises three screw holes 24 arranged substantially along a line. The attachment structures 22, 26 also each comprises two members 56 that are offset with respect to the line on which the three remaining members 56 are disposed. Each bridge 60 of the offset members 56 is inclined with respect to the mating direction B substantially in the extension plane of the first and second sections 12, 14. This inclination is approximately 45 degrees with respect to the mating direction B. Thus, the screw holes 24 of the first and second sections 12, 14 of the fifth embodiment approximately constitute an elliptical shape when the first and second sections 12, 14 adapt the closed configuration as illustrated in FIG. 10.

Two apertures 28, each associated with one of the holding members 16, are disposed along the junction 20. In this configuration, the apertures 28 are through openings extending through the entire width of the first and second sections 12, 14 in a normal direction with respect to the extension plane of the fixation assembly 10. The holding members 16 are centrally disposed within the apertures 28.

The apertures 28 of the fifth embodiment are jointly constituted by the first and second sections 12, 14. However, the apertures 28 may be offset with respect to the junction 20 in the mating direction B. In other words, the apertures 28 may each be disposed in one of the first and second sections 12, 14.

The holding members 16 of the fifth embodiment are constituted by pins (or wires) extending through the entire width of the first and second sections 12, 14 substantially along the mating direction B. The pins 16 may be welded or otherwise attached to the first and second sections 12, 14. Thus, the pins 16 do not come loose from the first and second sections 12, 14 when cut open. Furthermore, due to the welding of each pin 16, a simultaneous engagement of the first and second sections 12, 14 substantially along the mating direction B is realized.

As an alternative configuration, the holding members 16 may be constituted by screw nut assemblies extending in the mating direction B. The head of the screw may abut against the lateral outer surface of one of the first and second sections 12, 14 and the nut may abut against the lateral outer surface of the other one of the first and second sections 12, 14. The nut may further be fixed with respect to, or integrated with, one of the first and second sections 12, 14. The screw may in turn be longitudinally fixed with respect to one of the first and second sections 12, 14. Thus, each screw nut assembly simultaneously engages the first and second sections 12, 14 substantially along the mating direction B.

FIG. 11 shows the first and second section 12, 14 of the fifth embodiment in a separated configuration. As can be seen in the drawing, the first section 12 comprises a plurality of protrusions 34 in form of pins extending substantially in the mating direction B. The second section 14 comprises a plurality of recesses 36 each configured to accommodate one of the pins 34. The pins 34 may be formed as integral parts of the first section 12, for example through injection molding. Thus, the mating arrangement 32 is configured to rotationally lock the first and second sections 12, 14 relative to each other in the predetermined relative position against rotation about an axis substantially parallel with the mating direction B.

The pins 34 and the recesses 36 are aligned along a line in a plane perpendicular to the mating direction B. Thus, the pins 34 and the recesses 36 define a predetermined relative position between the first and second sections 12, 14 and prevent rotational movement between the first and second sections 12, 14 in the predetermined relative position about an axis substantially parallel with the mating direction B. In other words, relative rotation of the first and second sections 12, 14 in direction D is prevented by the pins 34 and recesses 36.

Figure 12:
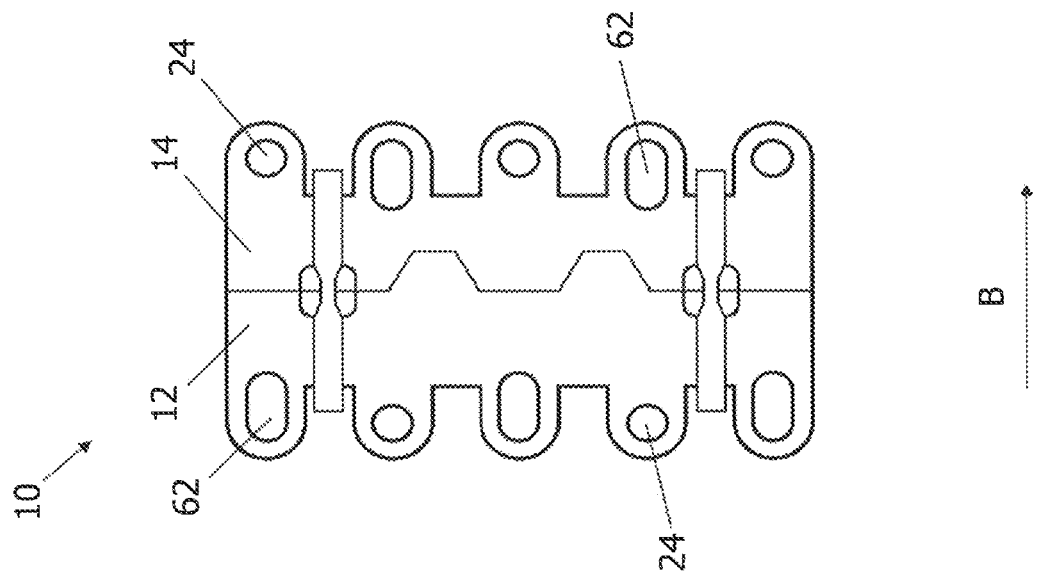
FIG. 12 shows a fixation assembly according to a sixth embodiment in a connected configuration.

FIG. 12 shows a fixation assembly 10 according to a sixth embodiment in a connected configuration. The attachment structures 22, 26 are the same as for the fifth embodiment. The fixation assembly 10 comprises a holding member 16 in form of a clip 16 as described in connection with the second embodiment. The first and second sections 12, 14 comprise traces for receiving the clip 16 aligned with the laterally outer surfaces of the first and second sections 12, 14. Furthermore, the traces in the first and second sections 12, 14 receive the clips 16 such that the clips 16 are flush with the upper surfaces 18 of the first and second sections 12, 14.

The apertures 28 are realized as blind openings. In other words, the apertures 28 extend from the upper surfaces in a direction parallel with a normal of the extension plane of the fixation assembly 10 through only a part of the first and second sections 12, 14. Also in the sixth embodiment, the apertures 28 may be laterally offset with respect to the junction 20.

The mating arrangement 32 of the sixth embodiment comprises a plurality of protrusions 34 having a cross-shape and a plurality of recesses having a shape corresponding to the protrusions 34. In this manner, each of the cross-shaped protrusions 34 cooperates with the corresponding recess such that the first and second sections 12, 14 are rotationally locked relative to each other in the predetermined relative position against rotation about an axis substantially parallel with the mating direction B.

Figure 13:
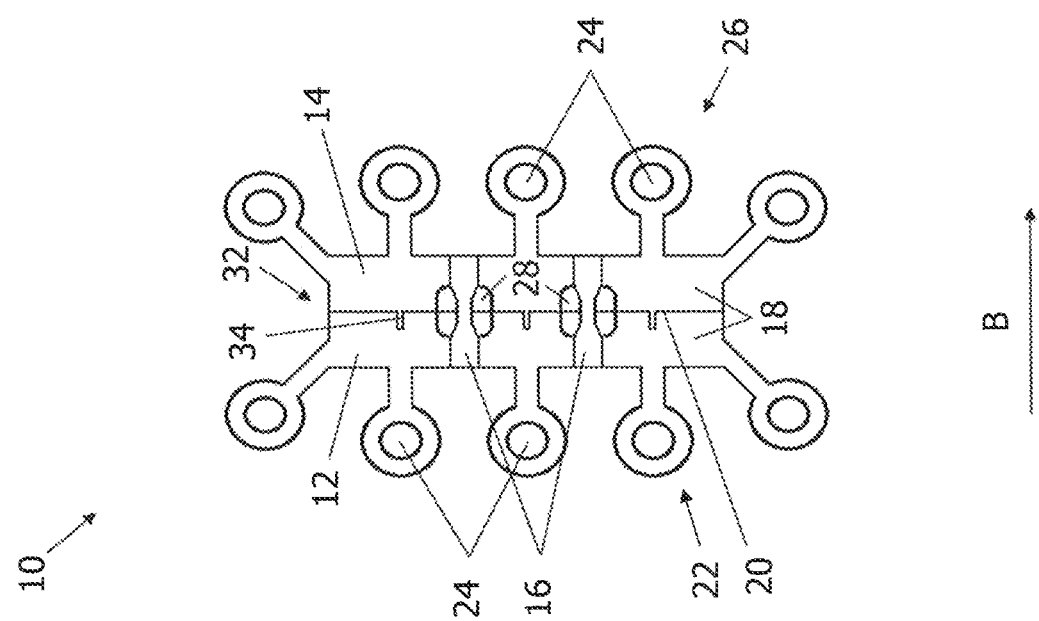
FIG. 13 shows a fixation assembly according to a seventh embodiment in a connected configuration.

FIG. 13 shows a fixation assembly 10 according to a seventh embodiment in a connected configuration. The first and second sections 12, 14 each comprises a plurality of openings formed as elongated holes 62. Each of the elongated holes 62 includes an inclined surface which is inclined with respect to the mating direction B by 45 degrees while maintained in a plane comprising the mating direction B and the normal of the extension plane of the fixation assembly 10. In this realization, the elongated holes 62 are unthreaded. Alternatively, the elongated holes 62 may have a thread. Thus, each elongated hole 62 is configured to exert a force on the opposite section 12, 14 when a bone screw is screwed through the elongated hole to the sternum.

The first and second sections 12, 14 also comprise a plurality of openings formed as screw holes 24 as generally described above with reference to FIG. 1 that extend substantially parallel with the normal of the extension plane of the fixation assembly 10. Further, as shown in FIG. 13, each screw hole 24 has a circular shape. For each elongated hole 62, a circular screw hole 24 is disposed on the opposite section along the mating direction B. For each section 12, 14, the elongated holes 62 and the circular screw holes 24 are substantially aligned along a common line.

As can further be seen in FIG. 13, the fixation assembly 10 comprises an alternate arrangement of circular screw holes 24 and elongated holes 62. That is, the first, third and fifth holes of the first section 12 and the second and fourth holes of the second section 14 are elongated holes 62 while the second and fourth holes of the first section 12 and the first, third and fifth holes of the second section 14 are circular screw holes 24. As an alternative to elongated holes 62, oblong holes may be provided.

At least one of the openings formed as circular screw holes 24 or elongated holes 62 may have a conical taper which substantially tapers inwardly in a direction towards a bone contacting surface of the first or second section 12, 14 in a conical fashion. Alternatively, the at least one circular screw hole 24 or elongated hole 62 may have a convex or spherical taper, i.e. has a curved shape. The taper may form a countersink. Moreover, the taper may extend over the full circumference of the holes 24, 62. Alternatively, the taper may extend over an arc segment of the circumference of the holes 24, 62. Further, at least one elongated hole 62 may have an inclined surface onto which a bone fastener is able to slide in a fastening or compression position. The taper or the inclined surface may be configured to receive a curved-shaped head of a bone fastener.

A cone angle of the taper or the inclined surface of the circular screw holes 24 or elongated holes 62 may generally be between 1 degree and 80 degrees, and is approximately 45 degrees in the present embodiment. Thus, the circular screw hole 24 or the elongated hole 62 may, on the one hand, adapted to slidingly receive bone fasteners (such as sliding or compression screws), and, on the other hand, adapted to receive a locking screw or a cortical screw. In case of a locking screw, a threaded head thereof mates with a locking feature of the circular screw hole 24 or elongated hole 62 for providing an angularly stable locking engagement therebetween at a pre-defined angle (i.e., monoaxially).

At least one of the openings formed as circular screw holes 24 or elongated holes 62 may include a locking feature configured to lock a bone fastener to the first or second section. Locking features may be provided in one or more of the holes 24 for receiving bone fasteners substantially perpendicular to bone and of the elongated or oblong holes 62. The locking feature may include a threaded adapted to engage a bone fastener. In the present embodiment, the locking feature is formed as a thread, e.g., a threaded hole portion. Alternatively, or in addition, the locking feature may be formed as one or more circumferential lips, as a bayonet-type feature or otherwise. The threaded portion of the locking feature is adapted to engage a bone fastener, e.g., engage a threaded head of a bone fastener. Thus, each of the circular screw holes 24 or elongated holes 62 can have a circumferential thread or is partially threaded.

FIG. 14 shows a fixation assembly 10 according to an eighth embodiment in a connected configuration. Here, the two apertures 28 are apertures that are not circumferentially closed. The apertures 28 are jointly constituted by the first and second sections 12, 14. The apertures 28 extend through the entire width of the first and second sections 12, 14 in a normal direction with respect to an extension plane of the fixation assembly 10.

FIG. 15A shows a fixation assembly 10 according to a ninth embodiment in a connected configuration. In this embodiment, the holding members 16 are constituted by elongated flexible members in form of wires. Each elongated flexible member 16 engages a laterally outer surface of the first and second sections 12, 14.

FIG. 15B shows a detailed cross-sectional view of the fixation assembly 10 according to the ninth embodiment perpendicular to the mating direction B in FIG. 15A. As can be seen from FIG. 15B, the fixation assembly 10 comprises at least one receiving structure 98 configured to receive the holding member 16 which is, in the present embodiment, formed as an elongated flexible member, such as a wire. The receiving structure 98 is arranged on a bone contacting side of the fixation assembly 10. The receiving structure 98 may generally be provided in the first section 12 or the second section 14. In the present embodiment, the receiving structure 98 is jointly constituted by the first and second sections 12, 14.

The receiving structure 98 may be formed as a recess, an opening or a groove. In the present embodiment, the receiving structure 98 is formed as a groove. The receiving structure 98 has, in this embodiment, substantially a U-shape in cross-section. The receiving structure 98 extends substantially along the mating direction B. Thus, the receiving structure 98 may extend substantially perpendicular to the longitudinal axis of the fixation assembly 10. Hence, the receiving structure 98 extends substantially perpendicular to the extension plane of the first and second sections 12, 14 when in the predetermined relative position.

The fixation assembly 10 may comprise multiple receiving structures 98. Further, the at least one receiving structure 98 may be arranged at a central (middle) portion or at an outer portion (e.g., an end portion) of the fixation assembly 10. In the present embodiment, one receiving structure 98 is arranged close to each outer end portion of the fixation assembly 10. Thus, the fixation assembly 10 includes two receiving structures 98. The at least one receiving structure 98 may be configured to receive a surgical cable or wire (e.g., a Kirschner wire, K-wire) or another holding member. Alternatively, or in addition, the at least one receiving structure 98 may be configured to receive a further fixation assembly including a flexible elongated member. The further fixation assembly may be formed as a zip tie.

The receiving structure 98 is generally formed such that the bone contacting surface of the fixation assembly 10 is reduced, which can be advantageous for certain surgical scenarios. It will be appreciated that for reducing the bone contacting area of the fixation assembly 10 one or more structures similar to the receiving structure 98 may be provided in addition or as an alternative to the receiving structure 98. In other words, such additional or alternative structures (not shown) do not need to fulfill any receiving function with respect to a holding member.

Figure 16:
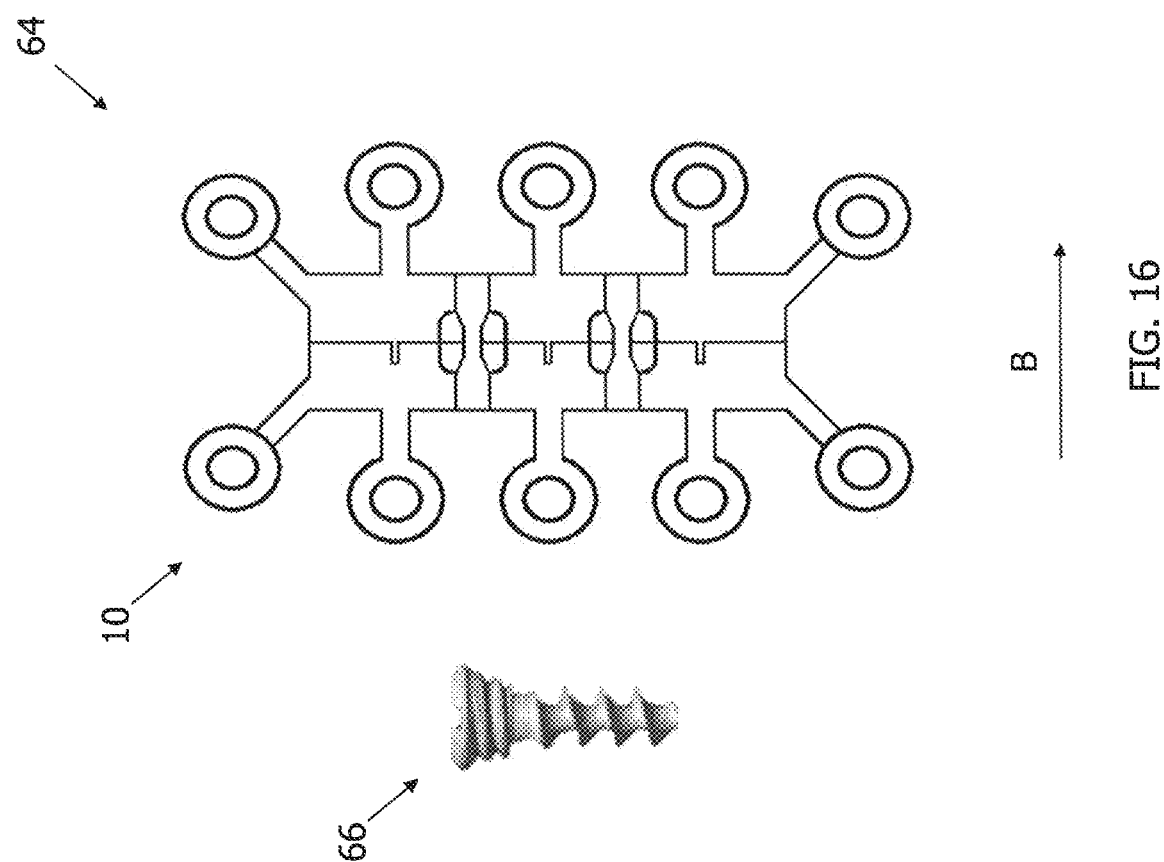
FIG. 16 shows a system comprising a fixation assembly.

FIG. 16 shows a system 64 comprising a fixation assembly 10 and a bone fastener 66 in form of a bone screw.

The bone screw 66 has a head and a shaft. The head of the bone screw has a thread. The thread of the head of the bone screw is configured to engage a thread 40 of one of the screw holes 24 or elongated holes 62 of the first or second section 12, 14 of a fixation assembly as previously described. As can be seen in FIG. 16, the head of the bone screw has a conical outer shape. Alternatively, the head may have a curved, e.g. convex or spherical, outer shape.

The shaft of the bone screw has a thread for engaging bone (e.g., a cancellous thread). In the present embodiment, the bone screw is formed as a locking screw. Alternatively, the bone screw can be a cortical screw, a compression screw or a bone peg.

The system 64 may comprise any previously described fixation assembly 10. Alternatively, or in addition, the system 64 may comprise a surgical tool for cutting the at least one holding member 16 open.

Figure 17:
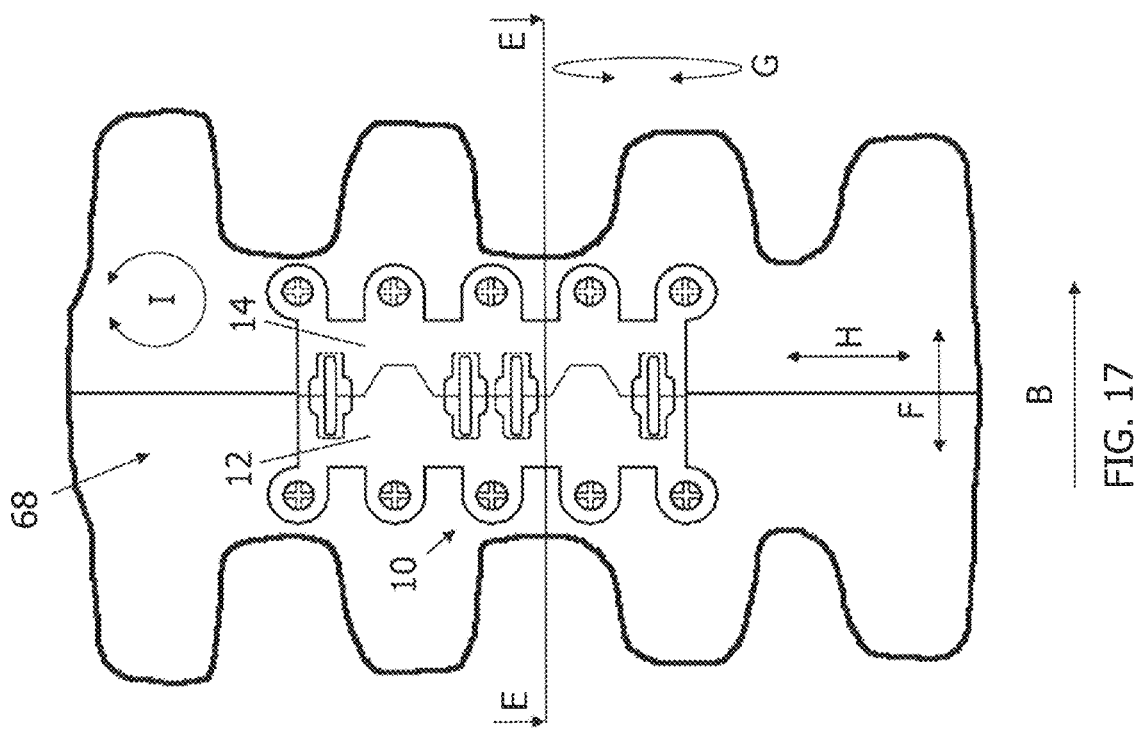
FIG. 17 shows a fixation assembly attached to a sternum.

FIG. 17 shows a fixation assembly 10 that has been attached to a sternum 68 with bone screws. The two sternum parts that had been separated by a bone cut have been brought back to their initial position and secured by the fixation assembly 10. The first section 12 is attached to one sternum part and the second section 14 is attached to the other sternum part.

During a period of coughing, a force acting on sternum 68 in a lateral direction F may be up to 1500 N. It is therefore desired to maintain the initially secured relative orientation of the sternum parts even when the sternum 68 is subjected to forces of this magnitude.

The closed configuration of the fixation assembly 10 prevents relative displacement of the sternum parts in the lateral direction F of the sternum 68 due to the at least one holding member 16 that holds the first and second sections 12, in the abutting relationship. By the provision of attachment structures 22, 26 having one or more elongated or oblong holes 62, the sternum parts can be additionally compressed in the lateral direction F upon tightening the associated one or more bone screws.

Furthermore, the mating arrangement 32 secured by the at least one holding member 16 contributes to the resistance against a relative rotation between the first and second sections 12, 14 about the lateral direction F, i.e., in a direction G. Thus, also the sternum parts are prevented from relative rotational displacement in direction G.

Since the first and second sections 12, 14 are held in a predetermined relative position in a plane perpendicular to the mating direction B, relative displacement of the sternum parts in a rostral/caudal direction H of the sternum 68 is suppressed. Additionally, the fixation assembly 10 prevents relative rotation between the first and second sections 12, 14 in the extension plane of the fixation assembly 10. Thus, relative rotation between the sternum parts in a direction I can be prevented.

Figure 18:
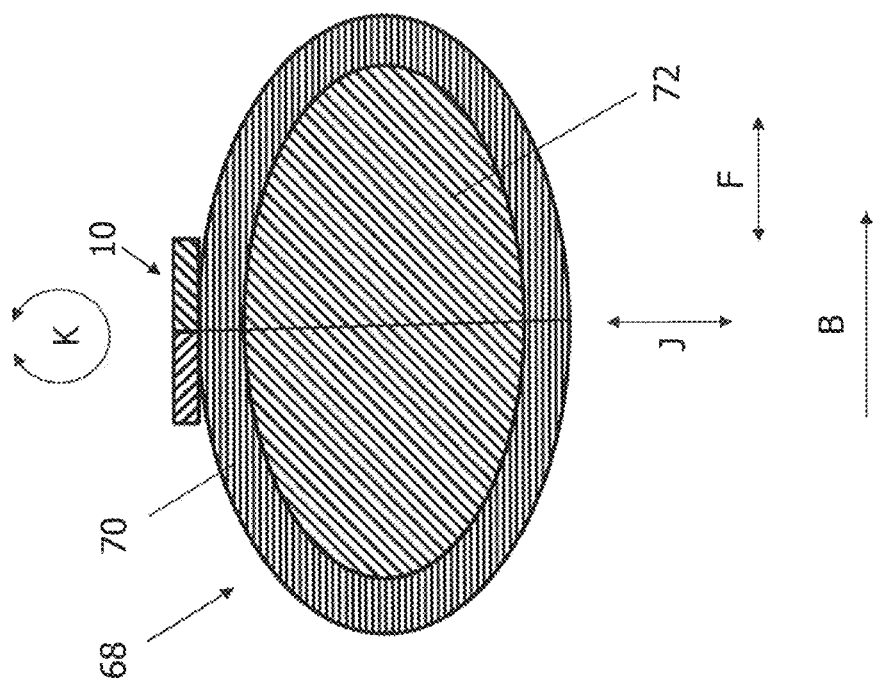
FIG. 18 shows a cross-sectional view of line E-E in FIG. 17.

FIG. 18 shows a cross-sectional view of line E-E in FIG. 17. The sternum 68 comprises cortical bone 70 and bone marrow 72. Due to the relatively thin layer of cortical bone 70, a proper alignment in an anterior/posterior direction J of the cortical bone faces is critical for the healing process. Since the first and second sections 12, 14 of the fixation assembly 10 are held in a predetermined relative position in a plane perpendicular to the mating direction B, the fixation assembly 10 also prevents relative displacement of the sternum parts in the anterior/posterior direction J.

The first and second sections 12, 14 of the fixation assembly 10 are further prevented from relative rotation in a direction K, i.e., in a direction about the rostral/caudal direction H. This rigidity contributes to maintain an initially applied compression between the sternum parts in the lateral direction F.

Referring to FIG. 19, there is shown a further embodiment 80 of an opening, e.g. a screw hole 24 or elongated hole 62, in form of a locking screw hole for the first or second section 12, 14 as discussed herein. The locking screw hole includes a lower cylindrical hole portion 82 on the bone contacting side of the first or second section 12, 14 and an upper cylindrical hole portion 84 on the side opposite to the bone contacting side. A middle portion 86 is arranged between the upper and lower cylindrical hole portion 82, 84. The middle portion 86 includes a circumferential lip 88 having roughly the shape of a triangle. Thus, in this embodiment, the locking feature of the holes 24, 62 is formed as a circumferential lip 88. A bone fastener 66 (not shown in FIG. 19) can be polyaxially inserted through the locking screw hole, wherein the bone fastener 66 lockingly engages the circumferential lip 88. As further illustrated in FIG. 19, a diameter of the middle portion 86 is smaller than each of a diameter of the upper cylindrical portion 84 and a diameter of the lower cylindrical portion 82. Moreover, the locking screw hole includes a supporting structure 90 defined by the upper cylindrical portion 84. The supporting structure 90 may receive a head portion of a bone fastener 66 (not shown in FIG. 19).

Figure 20:
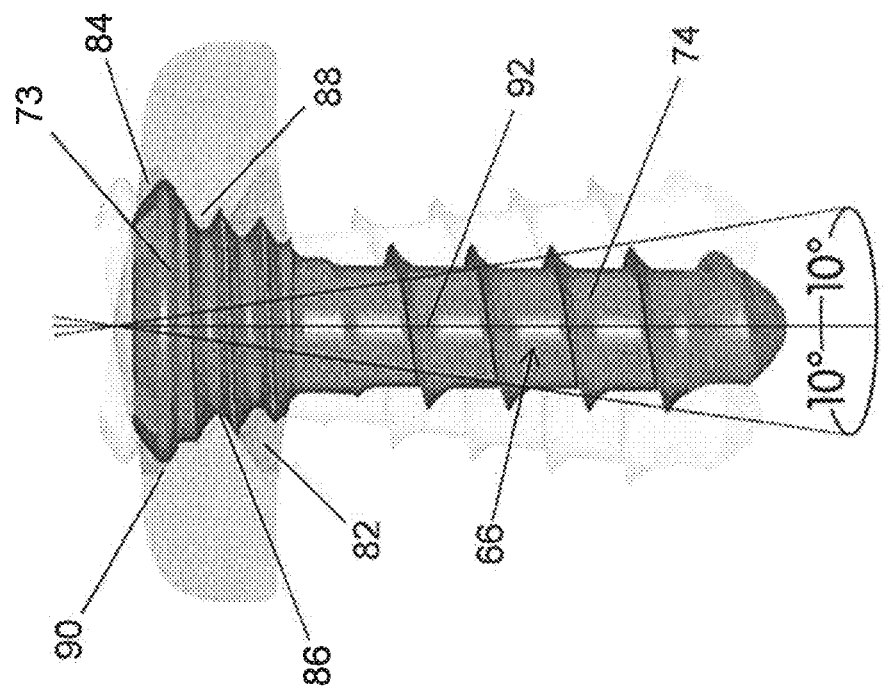
FIG. 20 is a view of the bone fastener embodiment shown in FIG. 16 inserted in the alternative locking screw hole embodiment of FIG. 19.

FIG. 20 shows a view of the bone fastener embodiment 66 shown in FIG. 16 inserted in the alternative locking screw hole embodiment 80 shown in FIG. 19.

As can be seen in FIG. 20, the bone fastener 66 can be inserted in the locking screw hole at different angles relative to an central axis 92 of the locking screw hole. Thus, an insertion angle of the bone fastener 66 may vary from about 0 to about 45 degrees (e.g., from about 0 to about 10 degrees) relative to the central axis 92 of the locking screw hole.

The thread of the head 73 of bone faster 66 is configured to engage on the circumferential lip 88 which has roughly the cross-sectional shape of a triangle. The bone fastener 66 can thus be polyaxially inserted through the locking screw hole, wherein the bone fastener 66 lockingly engages the circumferential lip 88.

Referring to FIG. 21 there is shown is a perspective view of a further embodiment 94 of an opening (e.g., a screw hole 24 or elongated hole 62) in form of a sliding screw hole for the first or second section 12, 14 as discussed herein. In the present embodiment, the sliding screw hole is formed as an elongated (e.g., oblong) hole.

The sliding screw hole includes a lower cylindrical hole portion 82 on the bone contacting side of the first or second section 12, 14 and an upper cylindrical hole portion 84 on the side opposite to the bone contacting side. In the present embodiment, the upper cylindrical hole portion 84 extends over an arc segment of the circumference of the sliding screw hole as shown in FIG. 21. The upper cylindrical hole portion 84 may extend over about 160 to about 260 degrees, e.g. about 160 to about 200 degrees, and in the present embodiment about 180 degrees.

The lower cylindrical hole portion 82 may include the locking feature as generally described above. Thus, the lower cylindrical hole portion 82 may have a thread or circumferential lip 88 configured to engage on a thread head 73 of a bone fastener 66 (not shown in FIG. 21).

A middle portion 86 is arranged between the upper and lower cylindrical hole portion 82, 84. The middle portion 86 includes a taper which substantially tapers inwardly in a direction toward a bone contacting surface of the attachment member in a conical fashion. In the present embodiment, the middle portion 86 also extends over an arc segment of the circumference of the sliding screw hole as shown in FIG. 21. The middle portion 86 may extend over about 160 to about 260 degrees, e.g. about 160 to about 200 degrees, and in the present embodiment about 180 degrees. The middle portion 86 may also include the locking feature as generally described above. Thus, the middle portion 86 may have a thread or circumferential lip 88 configured to engage on a thread head 73 of a bone fastener 66 (not shown in FIG. 21).

The sliding screw hole further includes an inclined surface 96 onto which a bone fastener 66 is able to slide in a fastening or compression position. Thus, the sliding screw hole may permit a bone fastener 66 to slide laterally or longitudinally with respect to the sliding screw hole. Further, the sliding screw hole may define a predetermined direction for a bone fastener 66. The inclined surface 96 has a predetermined angle with respect to an extension plane of the first or second section 12, 14 or with respect to the central axis of the sliding screw hole. The predetermined angle can be between about 20 and 70 degrees, for example about 40 to 50 degrees, and is, in the present embodiment, about 45 degrees. Moreover, the inclined surface 96 extends over an arc segment of the circumference of the sliding screw hole. Alternatively, the inclined surface 96 may extend over the full circumference of the sliding screw hole. The sliding screw hole may include two or more inclined surfaces 96 onto which a bone fastener 66 is able to slide in a fastening or compression position. One inclined surface 96 may be arranged within sliding screw hole opposite a further inclined surface 96. Thus, two inclined surfaces 96 may be arranged facing each other. The inclined surface 96 is configured to receive a curved or conical shaped head of a bone fastener 66. The bone fastener 66 may be a sliding screw, e.g., a compression screw.

Thus, a bone fastener 66 is able to slide (e.g., laterally or longitudinally) on the inclined surface 96 in a fastening or compression position. The sliding screw hole is thus configured to exert a force on the first or second section 12, 14 when a bone fastener 66 is screwed or inserted through the sliding screw hole into the sternum. Once, a bone fastener 66 in form of a locking screw inserted through the sliding screw hole has reached a fastening position, the threaded head 73 of locking screw 66 lockingly engages the locking feature (e.g., a thread or circumferential lip) of the lower cylindrical hole portion 82 of the sliding screw hole. Alternatively, when a bone fastener 66 in form of a sliding or compression screw inserted through the sliding screw hole has reached a compression position, the conical or curved head of bone fastener 66 abuts against the taper of the middle portion 86 of the sliding screw hole.

As described above, each of the first and second section 12, 14 may include an opening for receiving a bone fastener (e.g., a sliding screw hole as described above with reference to and as shown in FIG. 21). Thus, at least one sliding screw hole may be arranged in the first section 12 and at least one sliding screw hole may be arranged in the second section 14 of the fixation assembly. The sliding screw holes of the first and second section 12, 14 may be arranged opposite to each other. Further, the sliding screw holes of the first and second section 12, 14 may be facing each other. The inclined surfaces 96 of the sliding screw holes of the first and second section 12, 14 may extend substantially in a direction of the longitudinal axis of the fixation assembly or substantially perpendicular thereto. Thus, the inclined surfaces 96 of the sliding screw holes of the first and second section 12, 14 may extend substantially in the mating direction. Hence, the inclined surfaces 96 may substantially extend towards a cutting line of the sternum halves.

In one implementation, the sliding screw holes of the first and second section 12, 14 are arranged mirror-inverted with respect to a mirror axis. The mirror axis can be defined by the longitudinal axis of the fixation assembly or a line substantially perpendicular thereto. The mirror axis can be substantially perpendicular to the mating direction. Thus, the mirror axis may extend substantially along a cutting line of the sternum halves.

Consequently, a bone fastener 66 is able to slide on the inclined surface 96 of one of the sliding screw hole substantially in a direction towards the cutting line of the sternum halves (i.e., substantially in the mating direction) in a fastening or compression position. Thereby, the sternum halves are compressed to each other. The sliding screw hole is thus configured to exert a force on the fixation assembly and therewith on the two sternum halves when a bone fastener 66 is screwed or inserted through the sliding screw hole into the sternum.

The previously described embodiments of a fixation assembly 10 may be combined as desired. The different embodiments merely serve to illustrate various aspects of the present disclosure. For example, any described attachment structure 22, any described openings or holes 24, 62, any described holding member 16 and any described mating arrangement 32 may be used in all possible combinations.

While the present disclosure has been described with reference to exemplary embodiments, it will be appreciated that the present invention is not limited to what has been described above. For example, it will be appreciated that the dimensions of the parts may be varied as needed. Accordingly, it is intended that the present invention may be limited only by the scope of the claims appended hereto.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A fixation assembly for securing parts of a sternum, the assembly comprising:
a first section having a first attachment structure for securing the first section to a first sternum part; a second section having a second attachment structure for securing the second section to a second sternum part; a mating arrangement defining a mating direction and a predetermined relative position between the first and second sections in a plane perpendicular to the mating direction; and at least one holding member for detachably holding the first and second sections in an abutting relationship in the predetermined relative position, wherein the first and second sections are configured to abut against each other along a zig-zag junction in the predetermined relative position.

2. The fixation assembly according to claim 1, wherein the at least one holding member is configured to detachably hold the first and second sections in the abutting relationship in the predetermined relative position by simultaneous engagement of the first and second sections substantially along the mating direction.

3. The fixation assembly according to claim 1, wherein the assembly is configured to maintain the abutting relationship by engaging two substantially oppositely facing surfaces of the first and second sections with the at least one holding member.

4. The fixation assembly according to claim 1, wherein the assembly is configured to have the at least one holding member cut open by a surgical tool.

5. The fixation assembly according to claim 1, further comprising at least one aperture associated with the at least one holding member for facilitating access with a surgical tool to cut the at least one holding member when holding the first and second sections.

6. The fixation assembly according to claim 1, wherein the assembly is configured to establish the holding of the first and second sections by the holding member by a snap fit.

7. The fixation assembly according to claim 1, wherein the at least one holding member comprises a shape-memory material, and wherein the holding of the first and second sections by the holding member has been achieved by activation of the shape-memory material.

8. The fixation assembly according to claim 1, wherein the zig-zag junction is flush with an exterior surface of the fixation assembly in the predetermined relative position.

9. The fixation assembly according to claim 1, wherein the first or the second attachment structures comprises a circular, elongated or oblong hole configured to exert a force on the opposite section when a bone fastener is screwed through the hole to the sternum.

10. The fixation assembly according to claim 9, wherein the first and second sections each comprises an alternate arrangement of circular holes and elongated or oblong holes.

11. The fixation assembly according to claim 1, wherein at least one of the first and second attachment structures includes a locking feature configured to lock a bone fastener to the first or second attachment structure.

12. The fixation assembly according to claim 11, wherein the locking feature includes a threaded portion or one or more lips in a circumferential direction adapted to engage a bone fastener.

13. The fixation assembly according to claim 1, wherein at least one of the first and second sections is constituted by a bone plate.

14. A fixation assembly for securing parts of a sternum, the assembly comprising:

a first section having a first attachment structure for securing the first section to a first sternum part; a second section having a second attachment structure for securing the second section to a second sternum part; a mating arrangement defining a mating direction and a predetermined relative position between the first and second sections in a plane perpendicular to the mating direction; and at least one holding member for detachably holding the first and second sections in an abutting relationship in the predetermined relative position, wherein the first or the second attachment structures comprises a circular, elongated or oblong hole configured to exert a force on the opposite section when a bone fastener is screwed through the hole to the sternum, wherein the first and second sections each comprises an alternate arrangement of circular holes and elongated or oblong holes.

* * * * *